US012773192B2

(12) United States Patent
Acevedo et al.

(10) Patent No.: US 12,773,192 B2
(45) Date of Patent: Oct. 27, 2026

(54) MECHANISM TO WAKE A BATTERY IN A SURGICAL DEVICE

(71) Applicant: INSURGICAL, INC., Austin, TX (US)

(72) Inventors: Richard Acevedo, Austin, TX (US); Peter M Aman, Austin, TX (US); Philip Tetzlaff, Austin, TX (US); Aaron Jon Fowler, Leander, TX (US); Kevin R Simpson, Austin, TX (US)

(73) Assignee: INSURGICAL, INC., Austin, TX (US)

( * ) Notice: Subject to any disclaimer, the term of this patent is extended or adjusted under 35 U.S.C. 154(b) by 659 days.

(21) Appl. No.: 18/125,107

(22) Filed: Mar. 22, 2023

(65) Prior Publication Data

US 2023/0301640 A1 Sep. 28, 2023

Related U.S. Application Data

(60) Provisional application No. 63/322,956, filed on Mar. 23, 2022.

(51) Int. Cl.

| | |
|---|---|
| ***A61B 17/00*** | (2006.01) |
| ***H01M 10/42*** | (2006.01) |
| ***H01M 10/48*** | (2006.01) |

(52) U.S. Cl.

CPC ........... *A61B 17/00* (2013.01); *H01M 10/425* (2013.01); *H01M 10/4264* (2013.01);

(Continued)

(58) Field of Classification Search

CPC ... A61B 17/00; A61B 17/072; A61B 17/1628; A61B 2017/00115; A61B 2017/00221;

(Continued)

(56) References Cited

U.S. PATENT DOCUMENTS 6,126,670 A * 10/2000 Walker ................. A61B 17/142 173/217
2004/0092992 A1 * 5/2004 Adams ................... A61B 17/26 606/180

(Continued)

FOREIGN PATENT DOCUMENTS

EP 2921101 B1 7/2019
WO WO 2018-226945 A1 12/2018

OTHER PUBLICATIONS

International Searching Authority, International Search Report and Written Opinion dated Jul. 12, 2023 in International Application No. PCT/US2023/064871 (11 pages).

*Primary Examiner* — Amanda K Hulbert
(74) *Attorney, Agent, or Firm* — Trop, Pruner & Hu, P.C.

(57) ABSTRACT

A mechanism configured for use in a medical device, to wake a medical grade battery or medical grade battery pack from an inactive state may comprise a switch, an electrical circuit activated by a trigger mechanism, a pre-programmed timing event mechanism incorporated within the circuitry of the medical device or the battery or the battery pack itself, a wireless activation mechanism, an electromagnetic field mechanism, a magnetic field mechanism or a combination thereof, wherein said battery or the battery pack had been placed in an inactive state to preserve a battery charge until on-demand power levels were needed and the battery or the battery pack is re-activated or awakened when the wake mechanism is activated by an end user. A medical device and methods of use comprising mechanisms to wake a medical grade battery or medical grade battery pack from an inactive state to an active, normal or "on" mode.

14 Claims, 12 Drawing Sheets

(52) U.S. Cl.
CPC . *H01M 10/488* (2013.01); *A61B 2017/00734* (2013.01); *H01M 2220/30* (2013.01)

(58) Field of Classification Search
CPC .......... A61B 2017/00725; A61B 2017/00734; A61B 90/30; H01M 10/42; H01M 10/425; H01M 10/4264; H01M 10/488; H01M 2010/4271; H01M 2220/30
See application file for complete search history.

(56) References Cited

U.S. PATENT DOCUMENTS

| | | | | |
|---|---|---|---|---|
| 2006/0217729 | A1* | 9/2006 | Eskridge | A61B 17/162 606/80 |
| 2010/0312102 | A1* | 12/2010 | Barnes | A61B 17/3211 600/424 |
| 2014/0276654 | A1 | 9/2014 | Jenkins | |
| 2014/0276665 | A1 | 9/2014 | Lopez | |
| 2016/0022374 | A1 | 1/2016 | Haider et al. | |
| 2016/0249919 | A1* | 9/2016 | Savage | H01M 10/613 227/175.1 |
| 2018/0294655 | A1 | 10/2018 | Iwata et al. | |

* cited by examiner

MECHANISM TO WAKE A BATTERY IN A SURGICAL DEVICE

CROSS-REFERENCE

This application claims the benefit of U.S. Provisional Application No. 63/322,956, filed Mar. 23, 2022, which application is incorporated herein by reference.

BACKGROUND OF THE INVENTION

A typical battery-powered medical device is provided to a facility either; non-sterile, requiring a facility to provide pre-operative sterilization of the device; or sterile in a sealed package. When these devices are powered with a rechargeable battery, in most cases the battery is either attached to the tool prior to or at the time of surgery. Oftentimes, the batteries may not have a full charge, due to prolonged shelf storage time in the facility, or simply due to a failing battery charge memory. The facility which typically maintains and stores the rechargeable batteries, and usually the corresponding chargers, often fail to maintain these batteries and chargers in top working order or are unable to verify the quality or state of the battery's charge memory. Unfortunately, this often leads to older batteries that fail to have enough charge available to enable the devices in which they are employed to complete the procedures where they are being used, resulting in excess procedure times and cost.

In some scenarios, a battery may be provided inside the sterile device in a pre-charged state, allowing the device to be used immediately upon removal from the sterile packaging. Among the many challenges in this approach, is the length of time a battery can maintain its full charge while remaining in a sealed, sterile package for an extended period in storage prior to use.

As a result of high throughput requirements in most facilities, general maintenance is rarely done and preventative monitoring and maintenance is almost never done on this type of equipment. Hospital budgets for internal maintenance of equipment are generally geared toward high-end, multi-million dollar capital equipment such as x-ray and related radiological equipment. It is generally assumed that it is faster, simpler, and more economical for the hospital to wait for battery-powered instruments, such as drills, saws, reamers and their batteries to fail, then, send them back to the manufacturer for maintenance or replacement.

Thus it has become apparent that there is a need for an improved system for providing end users with cost-effective batteries with reliable charge levels which can provide the end user with a higher degree of efficiency, reduced downtime while reducing risk and keeping the costs of cleaning, maintenance, replacement and repair as low as possible.

SUMMARY OF THE INVENTION

During the recent COVID surges of 2020-2022, many devices and medical products having limited sterile shelf life, were rendered un-usable due to excessively long shelf life which exceeded the approved sterility shelf-life, after most elective surgeries were cancelled, postponed or deemed to be too high-risk as a result of the virulent transmissibility of the virus, especially in enclosed hospital settings. Among those items were sterile (and non-sterile) battery-powered devices with pre-packaged, integrated batteries and separately packaged sterile batteries. Hospitals and suppliers were forced in many cases to dispose of otherwise perfectly good devices and batteries because the quality of the battery charges could not be guaranteed or verified without breaking sterility. Further, many of those items could not be re-sterilized if opened, due to degradation of the device or components thereof that would occur as a result of repeated sterilization.

It has become apparent that there is a real need going forward to provide sterile battery-powered devices with batteries that can be placed in an inactive state after charging, then awakened when needed at some point in the future, with a certainty that a minimum level of maximum available charge will still be present at the time of awakening.

This disclosure relates generally to a mechanism for waking or activating a battery which had previously been put into an inactive state to preserve the stored power in the battery and maximize the potential useful battery shelf life. Although there may be many applications for such a mechanism, to date, this issue has not been adequately addressed for battery-powered medical devices or systems. More particularly, the issue has not been adequately addressed for pre-packaged, reusable, limited-use, or single-use sterile, battery-powered medical devices and systems such as medical or surgical tools provided to the operating room, with or without batteries pre-installed in the device.

One common means for providing batteries with many different items sold in commerce has been to insert a mylar strip, a circuit interruption strip or similar non-conducting material, between each active (fully awakened) battery end (cathode or anode) and one of the device contacts it is being shipped with. This then requires an end user to find the non-conducting material(s) and remove them in order to close a circuit and provide power to the device. Unfortunately, since the battery was fully awake, there will have been an active drain on the battery, (albeit a potentially low drain), the entire time it was in storage, in transit or sitting on a shelf, awaiting removal of the circuit interruption strip for activation and use. Further, the end user would have no idea how much of the original power was still available at the time the non-conducting material was removed and the circuit was initially closed. Quite often, depending on the battery design, transit time (often involving international shipping), and the time on the shelf, an end user would discover that the battery was dead or nearly dead-on-arrival.

A potential risk associated with battery use in medical devices includes the inability of the device to function for its intended use if a battery-related malfunction occurs, which is even more critical for life-sustaining devices. A review of Class I FDA recalls over a ten-year period (2005-2015) identified reasons for recalls related to batteries for medical devices that included reduced battery capacity, battery alarm failures, short-circuits indicating low battery, failure of battery to deliver, premature battery depletion, and battery undercharging. The medical device industry has also recently seen a transition in the use of "mature" battery technologies, such as lead-acid and nickel cadmium, to lithium (non-rechargeable) and lithium-ion (rechargeable) batteries. Likewise, there is a shortage of vendors that manufacture medical grade batteries specifically for non-implantable devices, which poses challenges with regard to the lack of appreciation for the quality and reliability required of batteries used in medical devices. (Medical Device Bulletin, Vol. 5, 2015)

Provided here is a mechanism to wake a medical tool battery or medical battery pack from an inactive state comprising: a switch on an exterior portion of a battery housing; or an electrical circuit, activated by a trigger mechanism; or a pre-programmed timing event mechanism incorporated within circuitry of the medical battery or medical battery pack; or a wireless activation mechanism; or an electromagnetic field mechanism; or a magnetic field mechanism; or a combination thereof, wherein said medical tool battery or medical battery pack comprises a medical grade battery that has been placed in an inactive state to preserve a battery or battery pack charge or minimize a power loss until an on-demand power level for the medical battery or medical battery pack is activated by an end user.

In some embodiments of the mechanism, an inactive state comprises: a SLEEP mode; or a LOW POWER mode; or a SHUTDOWN mode; or an ULTRA-LOW POWER mode; or a combination thereof.

In some embodiments of the mechanism, said medical tool battery or medical battery pack is provided integral with a sterile medical tool to an end user.

In some embodiments of the mechanism, said integral medical tool battery or medical battery pack is rechargeable.

In some embodiments of the mechanism, said integral medical tool battery or medical battery pack is disposable.

In some embodiments of the mechanism, said medical tool battery or medical battery pack is provided separately from a sterile surgical power tool to an end user.

In some embodiments of the mechanism, said separately provided medical tool battery or medical battery pack is provided in a sterile state.

In some embodiments of the mechanism, said separately provided medical tool battery or medical battery pack is provided in a non-sterile state.

In some embodiments of the mechanism, said separately provided medical tool battery or medical battery pack is rechargeable.

In some embodiments of the mechanism, said separately provided medical tool battery or medical battery pack is disposable.

In some embodiments, the mechanism further comprises a visual indicator to alert an end user about the medical tool battery or medical battery pack status.

In some embodiments, the mechanism further comprises an audible indicator to alert an end user about the medical tool battery or medical battery pack status.

In some embodiments of the mechanism, said medical tool battery or medical battery pack is rechargeable via an external cord attachment.

In some embodiments of the mechanism, said medical tool battery or medical battery pack is rechargeable via a wireless charging coil.

In some embodiments of the mechanism, said medical tool battery or medical battery pack is rechargeable via an external cord attachment.

In some embodiments of the mechanism, said medical tool battery or medical battery pack is rechargeable via a wireless charging coil.

In some embodiments of the mechanism, said mechanism is configured for a reusable medical tool battery or medical battery pack.

In some embodiments of the mechanism, said mechanism is configured for a limited-use medical tool battery or medical battery pack.

In some embodiments of the mechanism, said mechanism is configured for a single-use medical tool battery or medical battery pack.

In some embodiments of the mechanism, said mechanism is configured for use with a pre-packaged sterile, reusable, limited use or single-use medical device battery or medical battery pack.

Provided herein is a battery-powered medical device having a mechanism to wake a medical grade battery or medical grade battery pack from an inactive state comprising: a switch on an exterior portion of the medical device; or a switch on an exterior portion of a battery or battery pack housing; or an electrical circuit, activated by a trigger mechanism; or a pre-programmed timing event mechanism incorporated within the circuitry of the medical device; or a pre-programmed timing event mechanism incorporated within the circuitry of said medical grade battery or medical grade battery pack; or a wireless activation mechanism; or an electromagnetic field mechanism; or a magnetic field mechanism; or a combination thereof, wherein said medical grade battery or medical grade battery pack had been placed in an inactive state to preserve a battery charge until the wake mechanism is activated.

In some embodiments, said battery-powered medical device is provided to an end user in a sealed, sterile package.

In some embodiments, said battery-powered medical device further comprises an integrated medical grade battery.

In some embodiments, said battery-powered medical device is delivered to an end user without an integrated medical grade battery.

In some embodiments of said battery-powered medical device, said non-integrated medical grade battery is provided sterile, and separated from the battery-powered medical device in a second sealed, sterile package, either in or out of the battery-powered medical device sealed, sterile package.

In some embodiments of said battery-powered medical device, said non-integrated medical grade battery is provided non-sterile, and separately from the medical device.

In some embodiments of said battery-powered medical device, said battery-powered medical device is a reusable power tool.

In some embodiments of said battery-powered medical device, said battery-powered medical device is a limited-use power tool.

In some embodiments of said battery-powered medical device, said battery-powered medical device is a single-use power tool.

In some embodiments of said battery-powered medical device, said medical grade battery or medical grade battery pack inactive state comprises: a SLEEP mode; or a LOW POWER mode; or a SHUTDOWN mode; or an ULTRA-LOW POWER mode; or a combination thereof.

In some embodiments of said battery-powered medical device wherein said device is provided to an end user in a sealed, sterile package comprising an integrated battery, said medical grade battery is rechargeable.

In some embodiments of said battery-powered medical device wherein said device is provided to an end user without an integrated battery, said medical grade battery is rechargeable.

In some embodiments of said battery-powered medical device wherein said device is provided to an end user in a sealed, sterile package comprising an integrated battery, said medical grade battery is disposable.

In some embodiments of said battery-powered medical device wherein said device is provided to an end user without an integrated battery, said medical grade battery is disposable.

Some embodiments of said battery-powered medical device further comprise a visual indicator to alert an end user about the battery status.

Some embodiments of said battery-powered medical device further comprise an audible indicator to alert an end user about the battery status.

In some embodiments of said battery-powered medical device wherein said device is provided to an end user with an integrated battery, said medical grade battery is rechargeable via an external cord attachment.

In some embodiments of said battery-powered medical device wherein said device is provided to an end user without an integrated battery, said medical grade battery is rechargeable via an external cord attachment.

In some embodiments of said battery-powered medical device wherein said device is provided to an end user with an integrated battery, said device is provided to an end user in a sealed, sterile package comprising an integrated battery wherein said medical grade battery is rechargeable via a wireless charging coil.

In some embodiments of said battery-powered medical device wherein said device is provided to an end user without an integrated battery, said medical grade battery is rechargeable via a wireless charging coil.

In some embodiments of said battery-powered medical device, said medical grade battery-powered medical device comprises: a sterile surgical power drill; a sterile surgical power reamer; a sterile surgical power saw; a sterile dissection power tool; a sterile impaction power tool; a sterile retraction power tool; a sterile laparoscopic power tool; a sterile endoscopic power tool; a sterile stapling power tool; a sterile endoscopic power resection tool; a cautery tool; or a sterile head lamp.

Provided herein is a medical power tool comprising an integrated medical grade battery or battery pack previously placed in an inactive state; wherein said medical power tool comprises a wake mechanism configured to switch the medical grade battery from an inactive state to an active mode, said wake mechanism comprising: a switch on an exterior portion of the power tool; or an electrical circuit, activated by a trigger; or a pre-programmed timing event mechanism incorporated within the circuitry of the tool; or a pre-programmed timing event mechanism incorporated within the circuitry of the battery; or a wireless activation mechanism; or an electromagnetic field mechanism; or a magnetic field mechanism; or a combination thereof, wherein said medical grade battery had been placed in an inactive state to preserve a battery charge until the wake mechanism is activated.

In some embodiments of said medical power tool comprising an integrated medical grade battery or battery pack previously placed in an inactive state, said medical power tool is provided to an end user in a sealed, sterile package.

In some embodiments of said medical power tool comprising an integrated medical grade battery or battery pack previously placed in an inactive state, said medical power tool is a reusable power tool.

In some embodiments of said medical power tool comprising an integrated medical grade battery or battery pack previously placed in an inactive state, said medical power tool is a limited-use power tool.

In some embodiments of said medical power tool comprising an integrated medical grade battery or battery pack previously placed in an inactive state, said medical power tool is a single-use power tool.

In some embodiments of said medical power tool comprising an integrated medical grade battery or battery pack previously placed in an inactive state, said battery inactive state comprises a SLEEP mode; or a LOW POWER mode; or a SHUTDOWN mode; or an ULTRA-LOW POWER mode; or a combination thereof.

In some embodiments of said medical power tool comprising an integrated medical grade battery or battery pack previously placed in an inactive state, said reusable power tool provided to an end user in a sealed, sterile package comprises a sterile surgical power drill; a sterile surgical power reamer; sterile surgical power saw; a sterile dissection power tool; a sterile impaction power tool; a sterile retraction power tool; a sterile laparoscopic power tool; a sterile endoscopic power tool; a sterile stapling power tool; a sterile endoscopic power resection tool; a cautery tool; or a sterile head lamp.

In some embodiments of said medical power tool comprising an integrated medical grade battery or battery pack previously placed in an inactive state, said medical grade battery or battery pack wake mechanism is activated from its inactive state when removed from the sealed, sterile package.

In some embodiments of said medical power tool comprising an integrated medical grade battery or battery pack previously placed in an inactive state, said medical grade battery or battery pack is awakened from its inactive state when the wake mechanism is activated by the end user at the time of use.

Provided herein is a surgical power tool comprising: a non-integrated medical grade battery or battery pack previously placed in an inactive state wherein said surgical power tool comprises a wake mechanism configured to switch the battery from an inactive state to an active mode, said wake mechanism comprising: a switch on an exterior portion of the power tool; or an electrical circuit, activated by a trigger mechanism; or a pre-programmed timing event mechanism incorporated within the circuitry of the tool; or a wireless activation mechanism; or an electromagnetic field mechanism; or a magnetic field mechanism; or a combination thereof, wherein said non-integrated medical grade battery had been placed in an inactive state to preserve a battery charge until placed in the surgical power tool and awakened by the surgical power tool wake mechanism.

In some embodiments of said surgical power tool comprising a non-integrated medical grade battery or battery pack previously placed in an inactive state, said non-integrated medical grade battery further comprises a pre-programmed timing event mechanism incorporated within the circuitry of the battery; or a wireless activation mechanism; or an electromagnetic field mechanism; or a magnetic field mechanism; or a combination thereof, wherein said medical grade battery had been placed in an inactive state to preserve a battery charge until activated by the battery activation mechanism.

In some embodiments of said surgical power tool comprising a non-integrated medical grade battery or battery pack previously placed in an inactive state, said surgical power tool is provided to an end user in a sealed, sterile package.

In some embodiments of said surgical power tool comprising a non-integrated medical grade battery or battery pack previously placed in an inactive state, said non-integrated medical grade battery is provided sterile, and separated from the surgical power tool, in the medical device's sealed, sterile package.

In some embodiments of said surgical power tool comprising a non-integrated medical grade battery or battery pack previously placed in an inactive state, said non-integrated medical grade battery is provided non-sterile, separate from the surgical power tool, and not in the medical device's sealed, sterile package.

In some embodiments of said surgical power tool comprising a non-integrated medical grade battery or battery pack previously placed in an inactive state, said surgical power tool is a reusable power tool.

In some embodiments of said surgical power tool comprising a non-integrated medical grade battery or battery pack previously placed in an inactive state, said surgical power tool is a limited-use power tool.

In some embodiments of said surgical power tool comprising a non-integrated medical grade battery or battery pack previously placed in an inactive state, said surgical power tool is a single-use power tool.

In some embodiments of said surgical power tool comprising a non-integrated medical grade battery or battery pack previously placed in an inactive state, said medical grade battery inactive state comprises: a SLEEP mode; or a LOW POWER mode; or a SHUTDOWN mode; or an ULTRA-LOW POWER mode; or a combination thereof.

In some embodiments of said surgical power tool comprising a non-integrated medical grade battery or battery pack previously placed in an inactive state, said surgical power tool comprises a sterile surgical power drill; a sterile surgical power reamer; a sterile surgical power saw; a sterile dissection power tool; a sterile impaction power tool; a sterile retraction power tool; a sterile laparoscopic power tool; a sterile endoscopic power tool; a sterile stapling power tool; a cautery tool; or a sterile endoscopic power resection tool.

In any embodiment of the wake mechanism comprising an activation mechanism, said activation mechanism is configured with a momentary activation mode; or a toggleable activation mode; or a permanent activation mode.

In any embodiment of the wake mechanism comprising an activation mechanism, said activation mechanism is configured to reactivate hibernating batteries integrated into medical devices using an initiating mechanism activated by: a trigger embedded switch, contact, or similar mechanism; or an exterior accessed button, switch, or similar mechanism; or an external magnetic contact; or an external key or pin; or a near field communication based signal; wherein the waking voltage is supplied by: the primary battery pack, an integrated secondary cell, a battery, batteries, or other power supply; or a primary cell; or an external charger, batteries, or other power supply; or a dedicated low power timer IC, or an integrated capacitor comprising: i. a timed circuit breakage via inline fuse; ii. a timed circuit breakage via transistor; or iii. a circuit breakage via mechanical means; wherein the circuit closure is either permanent or momentary.

Provided herein is a medical device battery or battery pack comprising a medical grade battery or battery pack previously placed in an inactive state; wherein said medical grade battery or battery pack comprises a wake mechanism configured to switch the medical grade battery from an inactive state to an active mode, said wake mechanism comprising a switch on an exterior portion of the medical grade battery or battery pack; or a switch on an exterior portion of a battery housing containing said battery or battery pack; or an interior electrical circuit, activated by a trigger exterior to said medical grade battery or battery pack; or an external electrical circuit, activated by a trigger exterior to said medical grade battery or battery pack; or a pre-programmed timing event mechanism incorporated within the circuitry of the medical grade battery or battery pack; or a pre-programmed timing event mechanism incorporated within the circuitry of a tool using said medical grade battery or battery pack; or a wireless activation mechanism; or an electromagnetic field mechanism; or a magnetic field mechanism; or a combination thereof, wherein said medical grade battery or battery pack had been placed in an inactive state to preserve a battery charge until the wake mechanism is activated.

In some embodiments of the medical grade battery or battery pack comprising a medical grade battery or battery pack previously placed in an inactive state, wherein said medical grade battery or battery pack is provided to an end user in a sealed, sterile package.

In some embodiments of the medical grade battery or battery pack comprising a medical grade battery or battery pack previously placed in an inactive state, wherein said medical grade battery or battery pack is configured for use in a reusable medical power tool.

In some embodiments of the medical grade battery or battery pack comprising a medical grade battery or battery pack previously placed in an inactive state, wherein said medical grade battery or battery pack is configured for use in a limited-use medical power tool.

In some embodiments of the medical grade battery or battery pack comprising a medical grade battery or battery pack previously placed in an inactive state, wherein said medical grade battery or battery pack is configured for use in a single-use medical power tool.

In some embodiments of the medical grade battery or battery pack comprising a medical grade battery or battery pack previously placed in an inactive state, wherein said medical grade battery or battery pack comprises a NORMAL active mode and an inactive state which comprises: a SLEEP mode; or a LOW POWER mode; or a SHUTDOWN mode; or an ULTRA-LOW POWER; or a combination thereof.

In some embodiments of the medical grade battery or battery pack comprising a medical grade battery or battery pack previously placed in an inactive state, wherein said medical grade battery or battery pack is configured for use in a sterile surgical power drill; a sterile surgical power reamer; a sterile surgical power saw; a sterile dissection power tool; a sterile impaction power tool; a sterile retraction power tool; a sterile laparoscopic power tool; a sterile endoscopic power tool; a sterile stapling power tool; a sterile endoscopic power resection tool; a cautery tool; or a sterile head lamp.

In some embodiments of the medical grade battery or battery pack comprising a medical grade battery or battery pack previously placed in an inactive state, wherein said medical grade battery or battery pack is provided to an end user in a sealed, sterile package, and wherein said medical grade battery or battery pack wake mechanism is awakened from its inactive state when removed from the sealed, sterile package.

In some embodiments of the medical grade battery or battery pack comprising a medical grade battery or battery pack previously placed in an inactive state, said medical grade battery or battery pack is awakened from its inactive state when the wake mechanism is activated by the end user at the time of use.

Provided herein is a transitionable medical-grade battery or battery pack for a battery-powered medical device comprising: a medical grade battery or battery pack capable of being transitioned between an inactive state and an active state; wherein said medical grade battery or battery pack or said battery-powered medical device comprises a wake mechanism configured to switch the medical grade battery from an inactive state to an active mode or returning it to an inactive state, said wake mechanism comprising: a switch on an exterior portion of the medical grade battery or battery pack; or a switch on an exterior portion of a battery housing containing said battery or battery pack; or an interior electrical circuit, activated by a trigger exterior to said medical grade battery or battery pack; or an external electrical circuit, activated by a trigger exterior to said medical grade battery or battery pack; an internal switch or electrical circuit within the battery-operated medical device, activated by a magnetic field mechanism exterior to said battery-operated medical device, or a pre-programmed timing event mechanism incorporated within the circuitry of the medical grade battery or battery pack; or a pre-programmed timing event mechanism incorporated within the circuitry of a tool using said medical grade battery or battery pack; or a wireless activation mechanism; or an electromagnetic field mechanism; or a magnetic field mechanism; or a combination thereof, wherein said transitionable medical grade battery or battery pack is configurable to be placed in an inactive state to preserve a battery charge until the wake mechanism is activated and brings the medical grade battery or battery pack into an active state; or wherein said transitionable medical grade battery or battery pack is configurable to be switched from an active state capable of discharging useful current to operate a battery-powered medical device a battery charge until the wake mechanism is deactivated and brings the medical grade battery or battery pack back to an inactive state.

In some embodiments of the transitionable medical-grade battery or battery pack for a battery-powered medical device, said wake mechanism is activated by a magnetic field embedded within packaging configured to hold or transport said medical grade battery or battery pack or said battery-powered medical device.

In some embodiments of the transitionable medical-grade battery or battery pack for a battery-powered medical device, said medical grade battery or battery pack is provided to an end user in a sealed, sterile package.

In some embodiments of the transitionable medical-grade battery or battery pack for a battery-powered medical device, said medical grade battery or battery pack is configured for use in a reusable medical power tool.

In some embodiments of the transitionable medical-grade battery or battery pack for a battery-powered medical device, said medical grade battery or battery pack is configured for use in a limited-use medical power tool.

In some embodiments of the transitionable medical-grade battery or battery pack for a battery-powered medical device, said medical grade battery or battery pack is configured for use in a single-use medical power tool.

In some embodiments of the transitionable medical-grade battery or battery pack for a battery-powered medical device, said medical grade battery or battery pack is configured for use in a single-use medical power tool.

In some embodiments of the transitionable medical-grade battery or battery pack for a battery-powered medical device, said medical grade battery or battery pack comprises a NORMAL active mode and an inactive state which comprises: a SLEEP mode; or a LOW POWER mode; or a SHUTDOWN mode; or an ULTRA-LOW POWER; or a combination thereof.

In some embodiments of the transitionable medical-grade battery or battery pack for a battery-powered medical device, said medical grade battery or battery pack is configured for use in: a sterile surgical power drill; a sterile surgical power reamer; a sterile surgical power saw; a sterile dissection power tool; a sterile impaction power tool; a sterile retraction power tool; a sterile laparoscopic power tool; a sterile endoscopic power tool; a sterile stapling power tool; a sterile endoscopic power resection tool; a cautery tool; or a sterile headlamp.

In some embodiments of the transitionable medical-grade battery or battery pack for a battery-powered medical device, said medical grade battery or battery pack wake mechanism is awakened from its inactive state when removed from the sealed, sterile package.

In some embodiments of the transitionable medical-grade battery or battery pack for a battery-powered medical device, said medical grade battery or battery pack is awakened from its inactive state when the wake mechanism is activated by the end user at the time of use.

Provided herein is a battery-powered medical device having a mechanism to wake a medical grade battery or medical grade battery pack from an inactive state comprising: a packaging component comprising a magnetic field mechanism capable of holding an activation switch in an open position while in contact with the battery-powered medical device, the medical grade battery or medical grade battery pack; wherein said medical grade battery or medical grade battery pack had been previously placed in an inactive or shutdown state.

In some embodiments of the battery-powered medical device having a mechanism to wake a medical grade battery or medical grade battery pack from an inactive state, the magnetic field mechanism comprises a permanent magnet; or an electromagnet; or a temporary battery.

In some embodiments of the battery-powered medical device having a mechanism to wake a medical grade battery or medical grade battery pack, when said battery-powered medical device with the mating medical device is replaced in said packaging component with the magnetic field mechanism, said medical grade battery or medical grade battery pack is deactivated and returned to an inactive state.

Provided herein is a battery-powered medical device having a mechanism to wake a medical grade battery or medical grade battery pack from an inactive state comprising: a packaging component comprising: a power source; packaging electrical contacts; and a switch; wherein said battery-powered medical device comprises: mating medical device electrical contacts configurable to mate with the packaging component electrical contacts; and wherein the medical device electrical contacts rest upon the packaging electrical contacts within the packaging component, and wherein when said switch is activated by an end-user, a voltage is applied to the medical device or medical grade battery or medical grade battery pack, activating said medical grade battery or medical grade battery pack from a previously shut down state.

In some embodiments, of the battery-powered medical device having a mechanism to wake a medical grade battery or medical grade battery pack from an inactive state comprising a packaging component wherein, when said battery-powered medical device with the mating medical device electrical contacts is replaced in said packaging component with the mating packaging electrical contacts, said medical grade battery or medical grade battery pack is deactivated and returned to an inactive state.

Provided herein is a medical device packaging component containing a magnetic field mechanism capable of holding a switch open or closed, as in FIG. 4B. When the medical device is removed from the packaging, the absence of the magnetic field allows for the switch to reverse its state and activate the battery from a previously shutdown state.

In some embodiments, when said battery-powered medical device with the mating medical device electrical contacts is replaced in said packaging component with the mating packaging electrical contacts, said medical grade battery or medical grade battery pack is deactivated and returned to an inactive state.

Provided herein is a medical device packaging component containing an external power source (i.e., battery), contacts, and a switch (i.e., button switch, toggle). The medical device, with mating contacts, rests in the packaging on the packaging contacts. When the switch on the packaging is activated, a voltage is applied to the medical device, activating the battery from a previously shutdown state.

In some embodiments, when said battery-powered medical device with the mating medical device electrical contacts is replaced in said packaging component with the mating packaging electrical contacts, said medical grade battery or medical grade battery pack is deactivated and returned to an inactive state.

Additional aspects and advantages of the present disclosure will become readily apparent to those skilled in this art from the following detailed description, wherein only exemplary embodiments of the present disclosure are shown and described, simply by way of illustration of the several modes or best mode contemplated for carrying out the present disclosure. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

Figure 1:
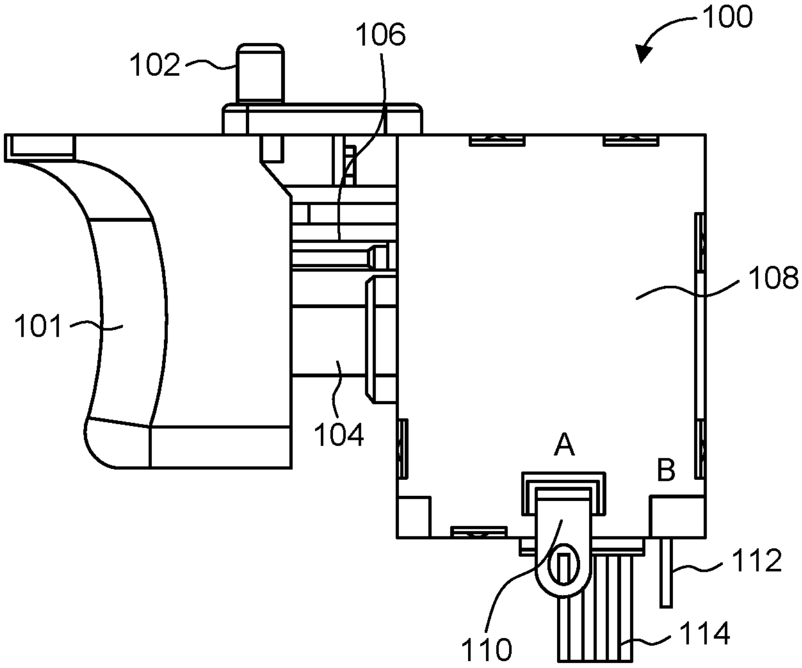
FIG. 1 is an embodiment of the trigger auxiliary switch assembly of a brushless trigger auxiliary wake-up switch mechanism for a medical battery, batteries, or battery pack.

The foregoing and other features of the present disclosure will become apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION OF THE INVENTION

Described herein are a plurality of mechanisms to wake a medical tool battery or battery pack from an inactive state. The mechanism may comprise a switch, an electrical circuit activated by a trigger mechanism, a pre-programmed timing event mechanism incorporated within the circuitry of a device, the battery, or battery pack itself, a wireless activation mechanism, an electromagnetic field mechanism, a magnetic field mechanism or a combination thereof, wherein a battery or battery pack having been placed in an inactive state to preserve a battery or battery pack charge until an on-demand power level is needed and the battery or battery pack is re-activated or awakened when the wake mechanism is activated by an end user.

In some embodiments, this specification describes medical devices and methods of use comprising mechanisms to wake or convert a battery's or battery pack's power-saving activity status from an inactive state to a "NORMAL" (or "ACTIVE") or "on" mode.

In still other embodiments, the battery wake mechanism is particularly important for sterile, pre-packaged medical devices and tools which may often have an unanticipated or unexpectedly long shelf-life. For example, during the recent COVID surges of 2020-2022, many devices and medical products having limited sterile shelf life, were rendered un-usable or expired due to excessively long shelf life which exceeded the approved sterility shelf-life, after most elective surgeries were cancelled, postponed, or deemed to be too high-risk as a result of the virulent transmissibility of the virus, especially in enclosed hospital settings.

Among those items were sterile (and non-sterile) battery-powered devices with pre-packaged, integrated batteries and separately packaged sterile batteries. Hospitals and suppliers were forced in many cases to dispose of otherwise perfectly good devices and batteries because the quality of the battery charges could not be guaranteed or verified without breaking sterility. Further, many of those items could not be re-sterilized if opened, due to degradation of the device or components thereof that would occur as a result of repeated sterilization.

Definitions as Used Herein

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range. In certain embodiments, the term "about" or "approximately" means within 40.0 mm, 30.0 mm, 20.0 mm, 10.0 mm 5.0 mm 1.0 mm, 0.9 mm, 0.8 mm, 0.7 mm, 0.6 mm, 0.5 mm, 0.4 mm, 0.3 mm, 0.2 mm, or 0.1 mm of a given value or range. In certain embodiments, the term "about" or "approximately" means within 5.0 kg, 2.5 kg, 1.0 kg, 0.9 kg, 0.8 kg, 0.7 kg, 0.6 kg, 0.5 kg, 0.4 kg, 0.3 kg, 0.2 kg, or 0.1 kg of a given value or range, including increments therein. In certain embodiments, the term "about" or "approximately" means within 1 hour, within 45 minutes, within 30 minutes, within 25 minutes, within 20 minutes, within 15 minutes, within 10 minutes, within 5 minutes, within 4 minutes, within 3 minutes within 2 minutes, or within 1 minute. In certain embodiments, the term "about" or "approximately" means within 60 seconds, within 45 seconds, within 30 seconds, within 25 seconds, within 20 seconds, within 15 seconds, within 10 seconds, within 5 seconds, within 4 seconds, within 3 seconds within 2 seconds, within 1.0 second, within 0.9 seconds, 0.8 seconds, 0.7 seconds, 0.6 seconds, 0.5 seconds, 0.4 seconds, 0.3 seconds, 0.2 seconds, 0.1 seconds, 0.09 seconds, 0.08 seconds, 0.07 seconds, 0.06 seconds, 0.05 seconds, 0.04 seconds, 0.03 seconds, 0.02 seconds, 0.01 seconds, 0.009 seconds, 0.08 seconds, 0.007 seconds, 0.006 seconds, 0.005 seconds, 0.004 seconds, 0.003 seconds, 0.002 seconds, or 0.001 seconds of a given value or range, including increments therein. In certain embodiments, the term "about" or "approximately" means within 20.0 degrees, 15.0 degrees, 10.0 degrees, 9.0 degrees, 8.0 degrees, 7.0 degrees, 6.0 degrees, 5.0 degrees, 4.0 degrees, 3.0 degrees, 2.0 degrees, 1.0 degrees, 0.9 degrees, 0.8 degrees, 0.7 degrees, 0.6 degrees, 0.5 degrees, 0.4 degrees, 0.3 degrees, 0.2 degrees, 0.1 degrees, 0.09 degrees. 0.08 degrees, 0.07 degrees, 0.06 degrees, 0.05 degrees, 0.04 degrees, 0.03 degrees, 0.02 degrees or 0.01 degrees of a given value or range, including increments therein. In certain embodiments, the term "about" or "approximately" means within 20.0 Amps, 15.0 Amps, 10.0 Amps, 9.0 Amps, 8.0 Amps, 7.0 Amps, 6.0 Amps, 5.0 Amps, 4.0 Amps, 3.0 Amps, 2.0 Amps, 1.0 Amps, 0.9 Amps, 0.8 Amps, 0.7 Amps, 0.6 Amps, 0.5 Amps, 0.4 Amps, 0.3 Amps, 0.2 Amps, 0.1 Amps, 0.09 Amps. 0.08 Amps, 0.07 Amps, 0.06 Amps, 0.05 Amps, 0.04 Amps, 0.03 Amps, 0.02 Amps or 0.01 Amps of a given value or range, including increments therein. In certain embodiments, the term "about" or "approximately" means within 30,000.0 mA, 20,000.0 mA, 10,000.0 mA, 1,000.0 mA, 900.0 mA, 800.0 mA, 700.0 mA, 600.0 mA, 500.0 mA, 400.0 mA, 300.0 mA, 200.0 mA, 100.0 mA, 90.0 mA, 80.0 mA, 70.0 mA, 60.0 mA, 50.0 mA, 40.0 mA, 30.0 mA 20.0 mA, 15.0 mA, 10.0 mA, 9.0 mA, 8.0 mA, 7.0 mA, 6.0 mA, 5.0 mA, 4.0 mA, 3.0 mA, 2.0 mA, 1.0 mA, 0.9 mA, 0.8 mA, 0.7 mA, 0.6 mA, 0.5 mA, 0.4 mA, 0.3 mA, 0.2 mA, 0.1 mA, 0.09 mA. 0.08 mA, 0.07 mA, 0.06 mA, 0.05 mA, 0.04 mA, 0.03 mA, 0.02 mA or 0.01 mA of a given value or range, including increments therein.

As used herein, and unless otherwise specified, the term "plurality," and like terms, refers to a number (of things) comprising at least one (thing), or greater than one (thing), as in "two or more" (things), "three or more" (things), "four or more" (things), etc.

As used herein, the terms "connected," "operationally connected," "coupled", "operationally coupled," "operationally linked," "operably connected," "operably coupled," "operably linked," and like terms, refer to a relationship (mechanical, linkage, coupling, etc.) between elements whereby operation of one element results in a corresponding, following, or simultaneous operation or actuation of a second element. It is noted that in using said terms to describe inventive embodiments, specific structures or mechanisms that link or couple the elements are typically described. In certain embodiments, the terms "connected," "operationally connected," "coupled", "operationally coupled," "operationally linked," "operably connected," "operably coupled," "operably linked," and like terms, refer to an electrical or electronic relationship, wherein there is a connection or coupling that facilitates a transfer of electrical energy from one circuit to another, or between parts of a circuit. For example, energy is transferred from a power source to an electrical load by means of conductive coupling, which may be either resistive or direct coupling. An AC potential may be transferred from one circuit segment to another having a DC potential by use of a capacitor. Electrical energy may be transferred from one circuit segment to another segment with different impedance by use of a transformer; this is known as impedance matching. These are examples of electrostatic and electrodynamic inductive coupling. However, unless otherwise specifically stated, when one of said terms is used, the term indicates that the actual linkage or coupling may take a variety of forms, which in certain instances will be readily apparent to a person of ordinary skill in the relevant technology.

As used herein, the terms "comprises," "comprising", or any other variation thereof, are intended to cover a nonexclusive inclusion, such that a process, method, article, or apparatus that comprises a list of elements does not include only those elements but may include other elements not expressly listed or inherent to such process, method, article, or apparatus.

As used herein, whenever the term "at least", "greater than", or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

As used herein, whenever the term "no more than", "less than", or "less than or equal to" precedes the first numerical value in a series of two or more numerical values, the term "no more than," "less than", or "less than or equal to" applies to each of the numerical values in that series of numerical values. For example, less than or equal to 3, 2, or 1 is equivalent to less than or equal to 3, less than or equal to 2, or less than or equal to 1.

As used herein, the terms "user", "end user" or "end-user" are interchangeably used. As used herein, and unless otherwise specified, these terms refer to a person or customer who ultimately uses or is intended to ultimately use a product. End users may or may not be "customers" in the usual sense; they are commonly employees of the customer. For example, if a large retail corporation buys a software package for its employees to use, even though the large retail corporation was the "customer" which purchased the software, the end users are the employees of the company, who will use the software at work. In an alternate example, hospitals which purchase power tools and medical devices for its employees (doctors and nurses) to use, even though the hospital was the "customer" which purchased the power tools and medical devices, the end users are the employees, doctors and nurses of the hospital, who will use the tools and medical devices in surgery.

As used herein, the term "proximity" means nearness in space or relationship, but not excluding the potential to be touching. Proximity is also alternatively meant to mean that one thing may be so close to another thing as to be "in direct or nearly direct contact" (in proximity) with another thing along some point. To "place something in proximity" is also meant to mean that items are "paired" or "mated together" either in their paired function or at some point of contact.

As used herein, and unless otherwise specified, the term "power tool", "medical tool", "equipment", "instrument", "devices" and similar terms refers to any type of battery-powered instrument commonly found in a hospital, surgical, or emergency medical setting. These may include, but are not limited to saws, drills, reamers, burring tools, cautery instruments, illuminating instruments, surgical robots and robotic tool accessories. This is not intended to be an exhaustive list, but merely an illustrative listing for the potential applications of this device and methods.

Further still, said battery powered medical device may further comprise sterile surgical equipment such as surgical staplers, robot assisted equipment, robotics, endoscopic and laparoscopic equipment, electrosurgery equipment, powered screwdrivers and potentially, any field hospital equipment such as suction tools, devices and systems and respiratory assist devices operated under battery or a battery back-up power device.

As used herein, and unless otherwise specified, the term "device", and similar terms refers to any device or tool requiring a battery, such as for a hospital, surgical, or emergency medical setting. Device may also refer to a power tool, such as a battery-powered power tool. In an embodiment, a device refers to medical device of any kind requiring a battery. In another embodiment, a device refers to a "sterile" medical device intended for a sterile medical procedure. In still a further embodiment, a device refers to a "sterile" medical power tool intended for a sterile medical procedure such as a surgical procedure. In yet another embodiment, a device refers to a "non-sterile" medical power tool intended for a sterile medical procedure such as a surgical procedure, following a suitable sterility protocol being done to prepare it for a sterile procedure.

As used herein, and unless otherwise specified, the term "battery", "battery pack", "charge pack" and similar terms interchangeably refer to a "medical grade" battery, (multiple) batteries or battery systems intended for use in any medical device or tool requiring a battery, such as for a hospital, surgical, or emergency medical setting, generally meeting the standards of the "bible" of the medical electrical equipment standards, ANSI/AAMI ES 60601-1, which outlines the general requirements for basic safety and essential performance of medical devices that require an electrical outlet or a battery, which is fully incorporated herein by reference. Medical Grade Batteries are distinguished herein as being different from commercial grade batteries used in commercial battery-powered tools such as those one might purchase in a hardware store. Furthermore, as used herein and unless otherwise specified, the term "battery" or "battery pack" and like terms means or refers to an energy source consisting of one or more electrochemical cells and terminals on both ends called an anode (−) and a cathode (+). Electrochemical cells transform chemical energy into electrical energy. As used herein, the batteries described are considered to be "secondary batteries", or "rechargeable batteries", that can be used more than once but have a set life expectancy. Because of their durability and ability to provide larger amounts of energy, rechargeable batteries are often used in larger devices such as laptops, tablets, and even cars. After a rechargeable battery exhausts its electrochemical energy, an external electric current can reverse the chemicals back into their original state, ready to repeat the cycle of electricity production all over again. Batteries of this type may be wet-cell or dry-cell batteries.

As used herein, and unless otherwise specified, the term "NORMAL mode", "ACTIVE mode" and similar terms refers to a high level of active peripheral circuits within the battery monitoring chip, that are drawing current, a battery discharge condition, wherein the DSG (Discharge) FET (Field-effect transistor) is ON. The battery control chip periodically monitors voltage, temperature and current (among other activities) on short intervals, i.e.: approximately every 10-250 ms. This mode allows on-demand use of the device and results in the highest level of current draw from the battery monitoring integrated circuit without needing to activate additional peripheral circuits within the integrated circuit.

As used herein, and unless otherwise specified, the term "SLEEP mode", "LOW-POWER mode" and similar terms refers to a mode where the number of active peripheral circuits within the battery monitoring chip that are drawing current may be reduced or minimized relative to "NORMAL mode", a battery discharge condition, wherein the DSG (Discharge) FET (Field-effect transistor) may be ON or OFF, and the monitoring interval is increased, i.e.: approximately 5 to approximately 255 seconds. A device in SLEEP state is returned to NORMAL state on-demand, in response to a triggering activity by the user, i.e.: pressing a button or switch. This allows the device to be transitioned from a power saving SLEEP mode to NORMAL mode.

As used herein, and unless otherwise specified, the term "SHUTDOWN mode", ULTRA-LOW-POWER mode" and similar terms refers to a battery state or condition, wherein, the DSG FET is OFF. The battery control chip functions are reduced or minimized, i.e.: only peripheral circuits within the battery monitoring chip required to exit SHUTDOWN mode are active. In this mode the battery cells are monitored at long intervals, i.e.: approximately 3 minutes to approximately 10 minutes, or monitoring is turned off. A device in SHUTDOWN mode may be returned to SLEEP mode or NORMAL mode on-demand via a triggering activity, i.e.: pressing a button or switch, application of external voltage, or internal timer. This allows the device to be transitioned from an ultra-low power SHUTDOWN mode to a battery cell monitoring SLEEP mode or NORMAL mode.

As used herein, and unless otherwise specified, the term "full charge", "minimum full charge", "useful full charge" and similar terms refers to a battery charge level having a voltage level of not less than 70% of the maximum rated voltage at full charge of the battery design or the required sufficient battery charge remaining to complete a procedure.

As used herein, and unless otherwise specified, the term "reusable" and similar terms mean or refer to a device that was designed and intended for long term, repeated use over an extended period of time.

As used herein, and unless otherwise specified, the phrase "limited use" and similar terms mean or refer to a device that was designed and intended for short term, repeated use over a limited period of time. Limited use devices are often intended for less than 10 repeated uses, and often less than that. Limited use items may also be recyclable or capable of being refurbished by the manufacturer to bring it back up to "new" status or at least some minimum acceptable standard.

As used herein, and unless otherwise specified, the terms "disposable," "single-use" and similar terms mean or refer to a device that was designed and intended for one application only. When labeled as "disposable," the product is intended to be, and likely should be discarded after its initial use. As used herein, "single-use" may also refer to a device that is either recyclable and/or has components capable of being refurbished by the manufacturer to bring it back up to "new" status or at least some minimum acceptable standard.

As used herein, and unless otherwise specified, the terms "mode", "state" and similar terms mean; have essentially the same meaning and are used interchangeably. In a classic dictionary definition; "Mode" is defined as an option allowing a change in the method of operation of a device. "State" is a noun which expresses the current status (or condition) of something which can sometimes be affected by the "mode" of a device. However, unless otherwise stated herein, "Mode" may also imply states that the user has put the device or devices into. Whereas "states" may also imply that the user has put the device or devices into that state or that the user is responsible for taking the device out of that state; or alternately, software or hardware incorporated into or associated with the device, may also put itself into different states under pre-determined conditions as determined by the software or firmware programming.

As used herein, and unless otherwise specified, the terms or phrases "Off mode," "dormant," "dormancy", "hibernation", "hibernate", "inactive", "inoperative", "a state of abeyance" or "in abeyance" and similar terms mean; a state in which a battery is essentially de-activated or rendered nearly inactive. Some battery types may utilize microchip circuitry to manage the state of the battery.

As used herein, and unless otherwise specified, the phrase "Sleep mode," also sometimes referred to as; "Stand By," "Suspend" and "Suspend to RAM" in computer terminology, and similar terms mean; a very low power mode, essentially pausing the state or activity of the device and temporarily suspending any unnecessary subsystems to a point where the reduced power state is just enough to enable the device operating system to retain the data for it to return to operation from the same point where it was "paused", when the device responds to a wake up event.

As used herein, and unless otherwise specified, any of the inactive states described above, may be considered to be different naming conventions that may represent a power state for a battery or battery pack, used to achieve a similar goal, which is to limit power drain from the battery pack when a medical tool is in an "inactive" or "dormant" mode, wherein there is no immediate need for power to activate the motor.

Further, as used herein, any of the inactive states described above may alternately all be descriptive names for modes which maintain a battery or battery pack in a sufficiently charged state to conduct a full procedure with full (100%) functionality of the device by maintaining an adequate charge on the battery in a non-functional mode, and then for the device to be removed from that mode and become fully functional.

As used herein, and unless otherwise specified, a "NORMAL" or "ACTIVE" mode, "permanent-activation mode", "fully functional mode" and similar terms mean; that the battery or battery pack used to provide on-demand power to a device has been awakened; switched "on" (versus "off"). The intent is that these terms refer to modes wherein a battery or battery pack is in a sufficiently charged mode to conduct a procedure with full (100%) functionality of the device in a functional mode; is fully functional and is in a mode or state that allows for power to be drawn from the battery or battery pack according to the medical power tools or device's designed conditions for use.

As used herein, and unless otherwise specified, the phrase "LOW POWER mode" and similar terms mean; a power mode that is less than fully available power in the "on-demand" state. It may best be described as a reduced power availability level provided to support only limited functions, such as power gage readings, voltage temperature and current etc. As used herein, a "LOW POWER mode" may indicate a charge level availability that is sufficient to support indications of status to the user, but not sufficient for functional operation of the device; for example, which could be less than 25% of the maximum rated voltage at full charge or insufficient battery charge remaining to complete a procedure.

As used herein, and unless otherwise specified, the term "integrated", and similar terms mean or refer to something that is incorporated into or with something else to make a complete unit. As used herein, a device may have a separable sub-component integrated into the packaging of the device, but not assembled to the device itself within the packaging. As such, the sub-component can be assembled by an end user once the combined unit packaging is opened.

As used herein, and unless otherwise specified, the term "mechanism" and similar terms mean or refer to a system of parts working together in a device; a piece of machinery, a circuit, or a mixed assembly comprising mechanical and electrical components: Further, as used herein, and unless otherwise specified, the term "mechanism" may also refer to an established process by which something takes place or is brought about. Finally, as used herein, and unless otherwise specified, the term "mechanism" may also refer to any combination of mechanical, chemical, electrical or electronic components, working either alone, in combination or a sequence of steps, to generate a desired action.

As used herein, and unless otherwise specified, the term "non-integrated" means or refers to something that is not incorporated into a complete assembly or assembled to make a complete unit. As used herein, a device may have another separable sub-component that is "non-integrated" or "not assembled" into the device itself creating a partially assembled device within the packaging when it is received by an end user. As such, a device may have a separable sub-component that is not in the packaging of the device and is packaged separately in its own packaging. As such, the sub-component can be assembled by an end user of the device once the two components are brought together. For example, a power saw may have the ability to be fitted with multiple types of saw blade chucks, each having a unique or special purpose capable of holding multiple types of saw blades. The same scenario would apply to drills and drill chucks. Further still, a similar scenario would apply to any battery powered device capable of receiving batteries having different power capabilities, sizes, sterile versus non-sterile, etc.

However, in some applications, such as single-use tools, "primary batteries", also known as nonchargeable batteries, which are considered to be disposable batteries can also be utilized.

Further still, in some embodiments, a capacitor can be used in place of a battery, (or a secondary battery), for example, in a wake-up circuit. A capacitor has a much higher charge and discharge rate than a battery, which is why a capacitor can be used in place of a battery when you need to make frequent power surges. The advantage of using a capacitor is that it will not lose its charge over time and can therefore be used for long periods without needing to be recharged.

As used herein, and unless otherwise specified, the term "transitionable" and similar terms mean or refer to a characteristic relating to or characteristic of a process or period of transition such as a battery capable of transitioning from a dormant or inactive state to an active state where it is capable of delivering current.

In view of this specification, it will be appreciated that there is a real need going forward to provide sterile battery-powered devices with batteries that can be placed in an inactive state after charging, then awakened when needed at some point in the future, with a certainty that a minimum functionally level of available charge will still be present at the time of awakening. The device should be 100% functional for the entire procedure, and the battery or battery pack should have retained sufficient charge to conduct the entire procedure for which it was designed and intended to perform.

This disclosure relates to a mechanism or assembly for waking or activating a battery or battery pack which had previously been put into a non-active or hibernate state, to preserve the stored power in the battery or battery pack and maximize the potential useful battery shelf life. Although there may be many applications for such a mechanism, to date, this issue has not been adequately addressed for battery-powered medical devices or systems. More particularly, the issue has not been adequately addressed for batteries, and in particular, medical-grade batteries used in pre-packaged, reusable, limited-use, or single-use sterile, battery-powered medical devices and systems, such as medical or surgical tools provided to the operating room, with or without batteries pre-installed in the device.

Referring now to the plurality of wake-up mechanisms and assemblies described herein:

As illustrated in FIG. 1, an embodiment of a battery wake-up mechanism is a brushless trigger wake-up switch mechanism 100 having a mechanical switch activation means, such as a pull trigger, configurable for any of the applications described herein.

The trigger wake-up switch mechanism 100 which may comprise a brushless trigger, may be incorporated into any medical power tool and can comprise a push or pull brushless trigger 101, which may be a multi-purpose component for waking the tool battery and activating the motor of the tool, a brushless trigger shaft 104 for mounting the brushless trigger to the tool, a brushless trigger guide 106 for brushless trigger directional control, and a directional switch 102, associated with the brushless trigger mechanism 100 for determining direction of a tool motor (i.e.: forward, reverse), that is ultimately being controlled by the switch, after the brushless trigger switch activates or wakes the battery.

Figure 2A:
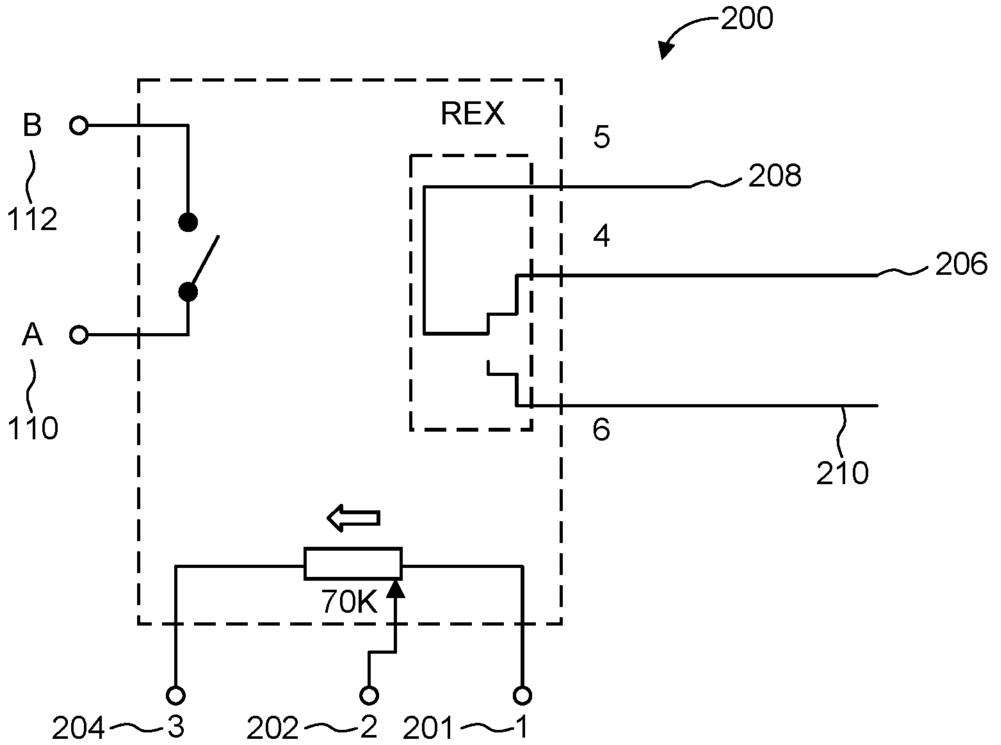
FIG. 2A is an embodiment of the simplified trigger electrical schematic of the brushless trigger auxiliary wake-up switch assembly for a medical battery, batteries, or battery pack.
Figure 2B:
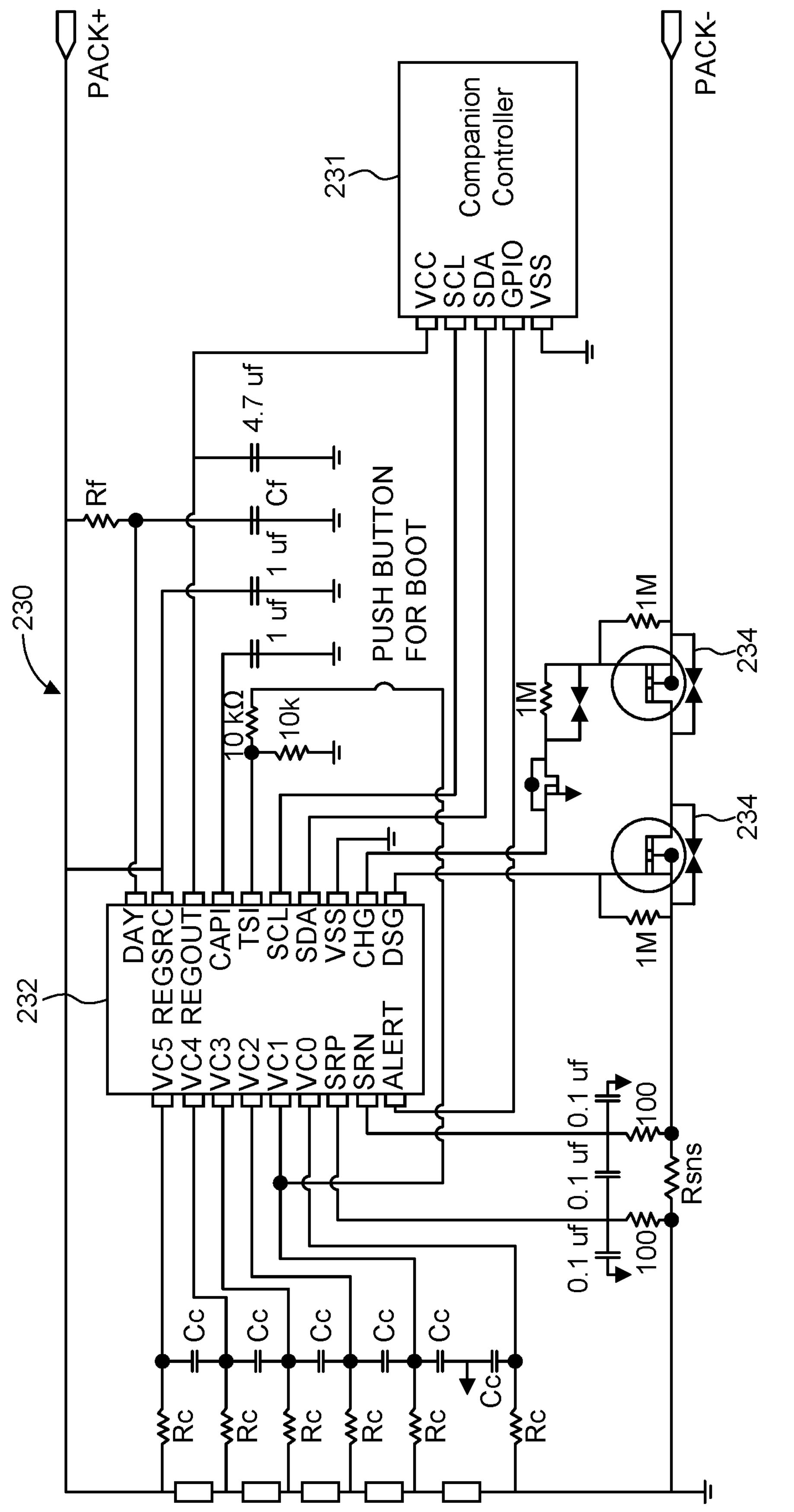
FIG. 2B is a detailed embodiment of a battery pack simplified electrical schematic of the brushless trigger auxiliary wake-up switch mechanism for a medical battery, batteries, or battery pack.
Figure 3:
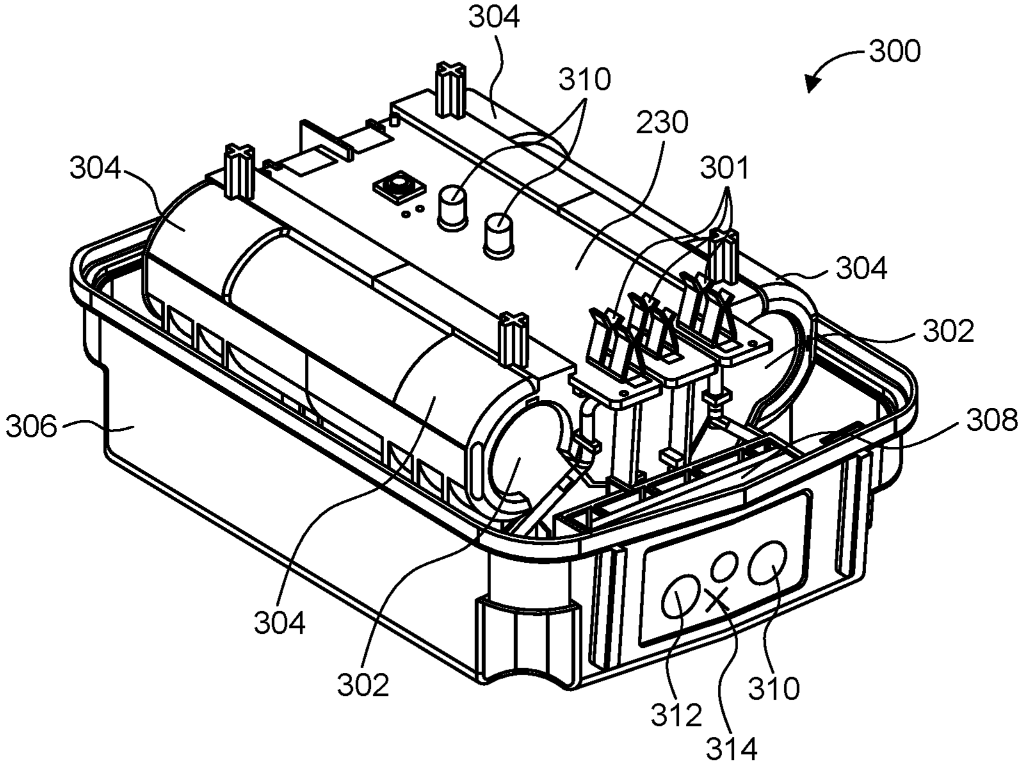
FIG. 3 is an embodiment of a battery pack with an external mechanical wake-up switch.

A further extension of the wake-up switch mechanism 100 may include a brushless trigger circuit housing 108, as further described in FIG. 2, which could comprise 2 or more safety contacts 110, 112 for opening/closing a circuit and a plurality of control leads 114 linked to a control circuit as illustrated in FIG. 3.

FIG. 2A is an embodiment of a brushless trigger electrical schematic 200 of the trigger circuit housing 108 for a battery wake-up switch mechanism 100. As shown here in FIG. 2A, the circuit schematic illustrated may comprise the safety contacts 110, 112 for opening/closing the circuit, a plurality of variable speed controls, 201, 202, 204 and a plurality of rotational controls 206, 208 and 210.

FIG. 2B is an embodiment of a medical battery pack simplified electrical schematic of a battery control board 230 for the battery wake-up mechanism. The control board 230 for the battery wake-up mechanism may reside on or about the battery or batteries within the battery pack contained within the battery housing of the tool, as further illustrated in FIG. 3. As illustrated herein, the control board, 230 comprises a communication chip 231 that is in communication with the trigger circuit 200, a battery protection chip 232 that is used for effective monitoring of the battery charge, discharge state, and under certain conditions to shut down the charge, discharge circuit to prevent damage to the battery, thus preserving the performance and service life of the battery. The control board further comprises a power MOSFET 234 (Metal-Oxide-Semiconductor Field Effect Transistor), to handle significant power levels within the circuit. MOSFETs have high speed and good efficiency at low voltages. MOSFETs may have an isolated gate that makes it easy to drive.

FIG. 3 is an example of a medical battery pack 300 with an external mechanical wake-up switch. As shown in this embodiment, the illustrative battery pack may comprise the battery control board 230 (sometimes but not necessarily exclusively located on or about the battery or batteries within the battery pack housing), contact springs 301 for providing power to the tool motor(s), the battery, or batteries 302 of the battery pack, a battery cradle 304 for securely holding the batter(ies) of the battery pack within the battery housing (lower half) 306, a "wake" control board 308, for controlling the wake circuit within the battery pack; a status panel 314, comprising a manual wake button 312 and a status light (LED) indicator 310. In addition, the control board 230 may also comprise one or more secondary status light (LED) indicators 310.

Figure 4A:
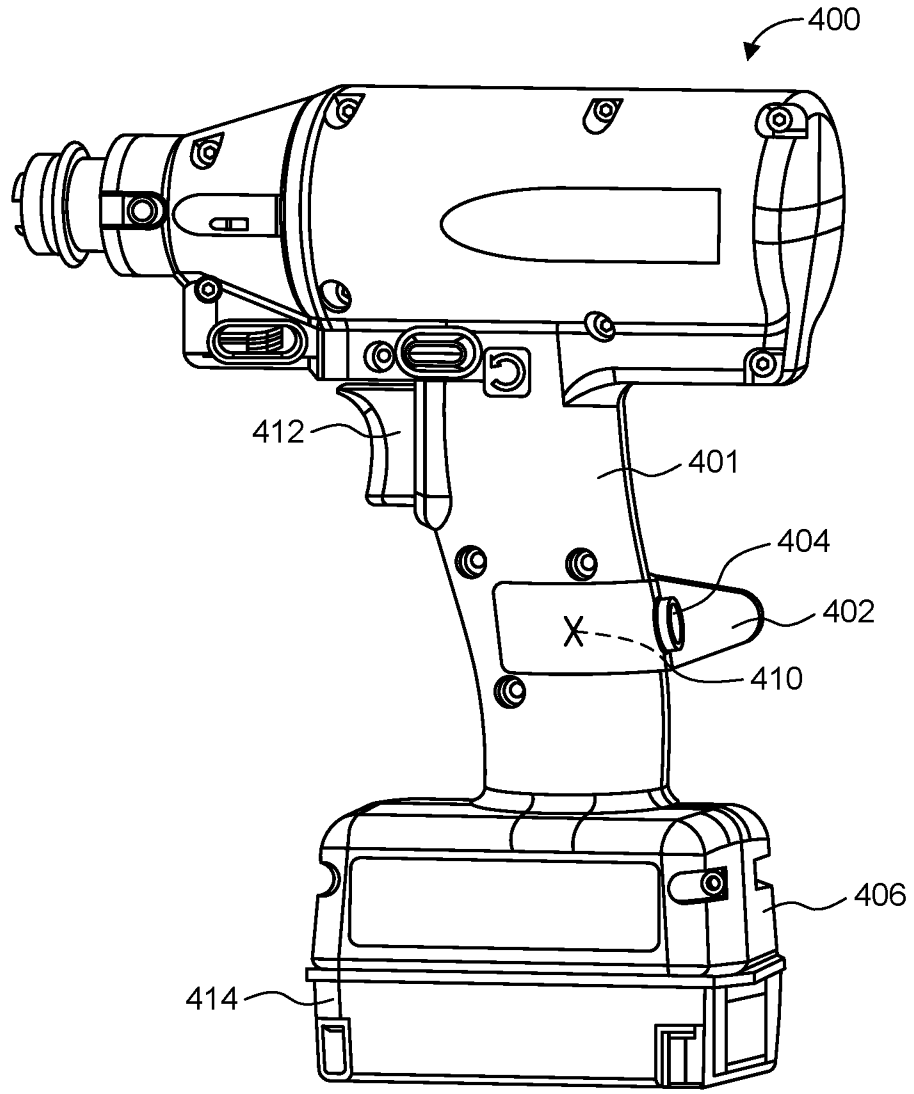
FIG. 4A is an illustration of a magnetic switch for a battery pack wake-up mechanism having a battery wake-up mechanism utilizing a magnetic clip or attachment on the handle of the tool having a magnetic pull force greater than a switch spring force, capable of holding an internal switch open until the magnet is removed.
Figure 4B:
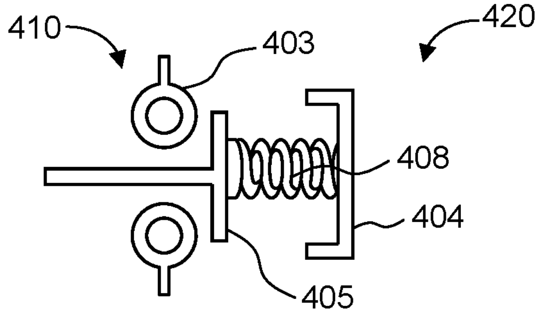
FIG. 4B is a schematic illustration of the magnetic switch for the clip attachment of FIG. 4A with the switch held open.

FIG. 4A is an illustrative embodiment of a medical power tool 400 having an activation trigger 412 to draw current for the drive motor and utilizing a magnetic clip 402 or similar attachment, affixed on the handle 401 of a tool, acting as a switch control for an internal battery wake switch 410 (not shown). In the current configuration with the magnetic clip 402 affixed, the magnetically activated switch 410 (internal to the handle) is held open by the magnet 404 mounted in the clip. As noted earlier, the magnet 404 may be any form of magnet with enough strength to overcome a spring force 408 of an internal switch, as illustrated in FIG. 4B. One such type of magnet may be a rare earth magnet. Alternatively, the scenario could be reversed, wherein the polarity of the clip and internal magnetic switch worked in reverse, such that the switch would be closed or activated by the attachment of a magnetic clip. Regardless of the scenario, when the switch is open, the power from a battery pack 300 contained within the battery pack housing 406, (upper half)/414 (lower half) remains dormant and is prevented from reaching the tool.

As illustrated in FIG. 4B is a general schematic of an open switch embodiment 420 comprising a magnetically operated single pole switch 410 with a single throw or actuator 405, the poles 403, a spring 408 and a magnet 404. In this embodiment, the magnetic clip 402 containing the magnet 404 is a battery wake-up mechanism, which, when attached to the tool, deactivates the battery or battery pack 320 by pulling the magnetic throw 405 away from the poles or contacts 403 of the switch and opening the switch, thus preventing them from making contact and carrying current, thus creating an open circuit. Alternatively, as previously described, the scenario could be reversed, wherein the polarity of the clip and internal magnetic switch worked in reverse, such that the switch would be closed or activated by the attachment of a magnetic clip.

Figure 5A:
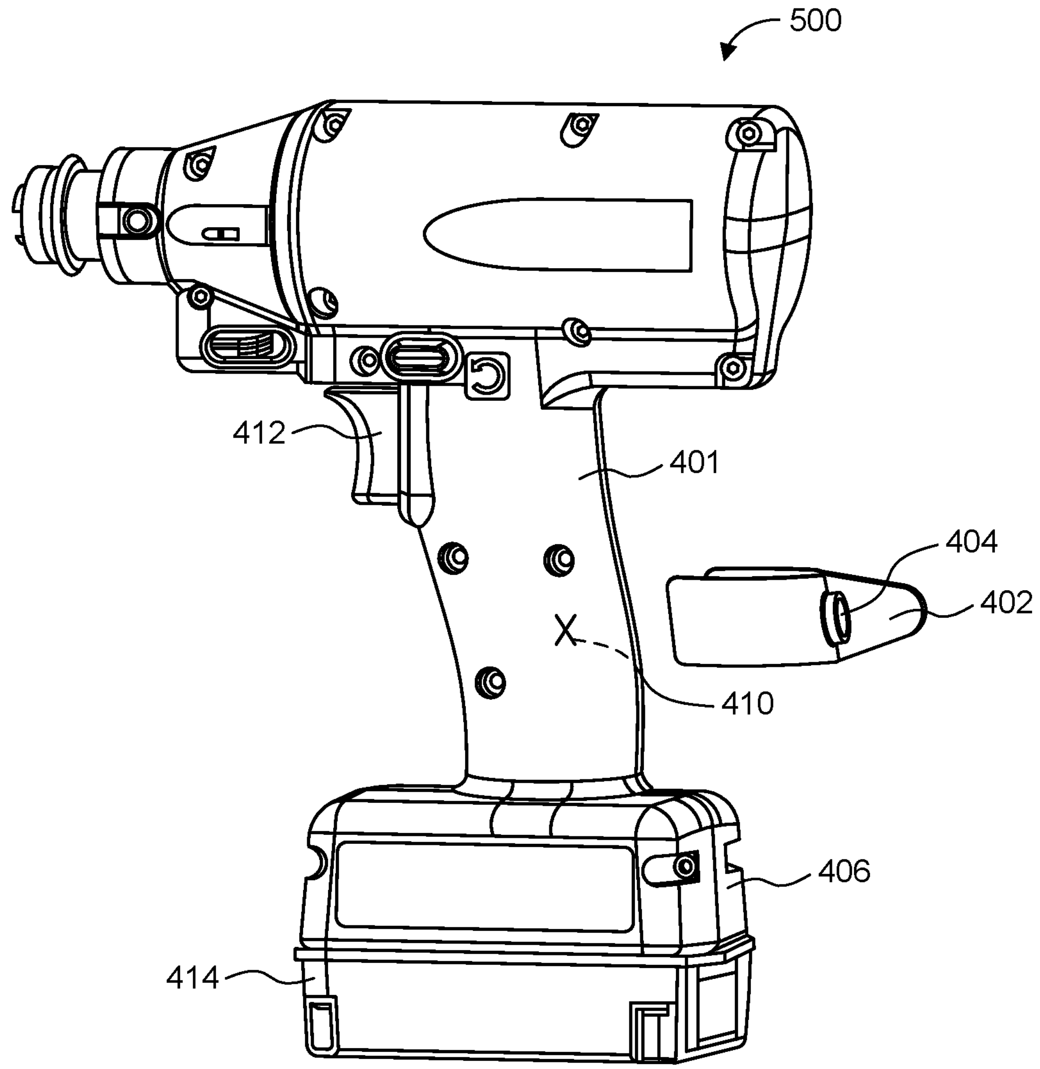
FIG. 5A is an illustration of the magnetic clip or attachment battery wake-up mechanism, removed from the tool, thus activating, or waking the battery or battery pack.
Figure 5B:
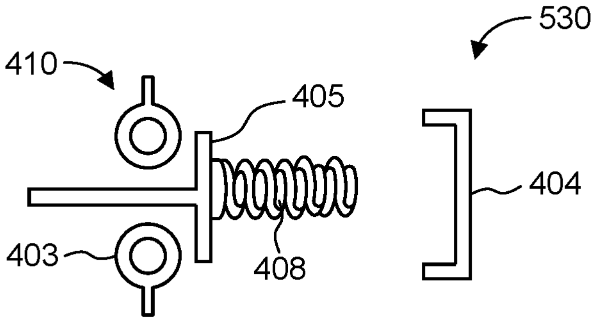
FIG. 5B is a schematic illustration of the magnetic switch for the clip attachment of FIG. 5A with the switch closed or activated.

FIG. 5A is an illustrative embodiment of a medical power tool 500 having an activation trigger 412 to draw current for the drive motor and utilizing a magnetic clip 402 or similar attachment, detached from the handle 401 of a tool, acting as a switch control for an internal battery wake switch 410 (not shown). In the current configuration with the magnetic clip 402 detached, the magnetically activated switch 410 (internal to the handle) is enabled to close by removal of the magnet 404 mounted in the clip. As noted earlier, the magnet 404 may be any form of magnet with enough strength to overcome a spring force 408 of an internal switch, as illustrated in FIG. 5B. One such type of magnet may be a rare earth magnet. Alternatively, the scenario could be reversed, wherein the polarity of the clip and internal magnetic switch worked in reverse, such that the (closed) switch would be opened or activated by the attachment of a magnetic clip. The internal magnetic switch having a magnetic pull force greater than a switch spring force, is capable of holding said switch open until the magnet is removed. Regardless of the scenario, when the switch is closed, the power from a battery pack 320 contained within the battery pack housing 406, (upper half)/414 (lower half) is awakened by the activating switch and is allowed to reach the tool with a full charge from the battery.

FIG. 5B is a general schematic of a closed switch embodiment 530 comprising a magnetically operated single pole switch 410 with a single throw or actuator 405, contacts or polls 403, a spring 408 and a magnet 404. In this embodiment, the magnetic clip 402 is a battery wake-up mechanism, which, when detached from the tool 500, activates the battery or battery pack by releasing the magnetic throw 405 and allowing it to connect the poles or contacts 403 of the switch, thus closing the switch, allowing them to carry current and creating a closed circuit. Once again, as previously described, the scenario could be reversed, wherein the polarity of the magnet and internal magnetic switch worked in reverse, such that the switch would be opened or deactivated by the attachment of a magnet.

Figure 6:
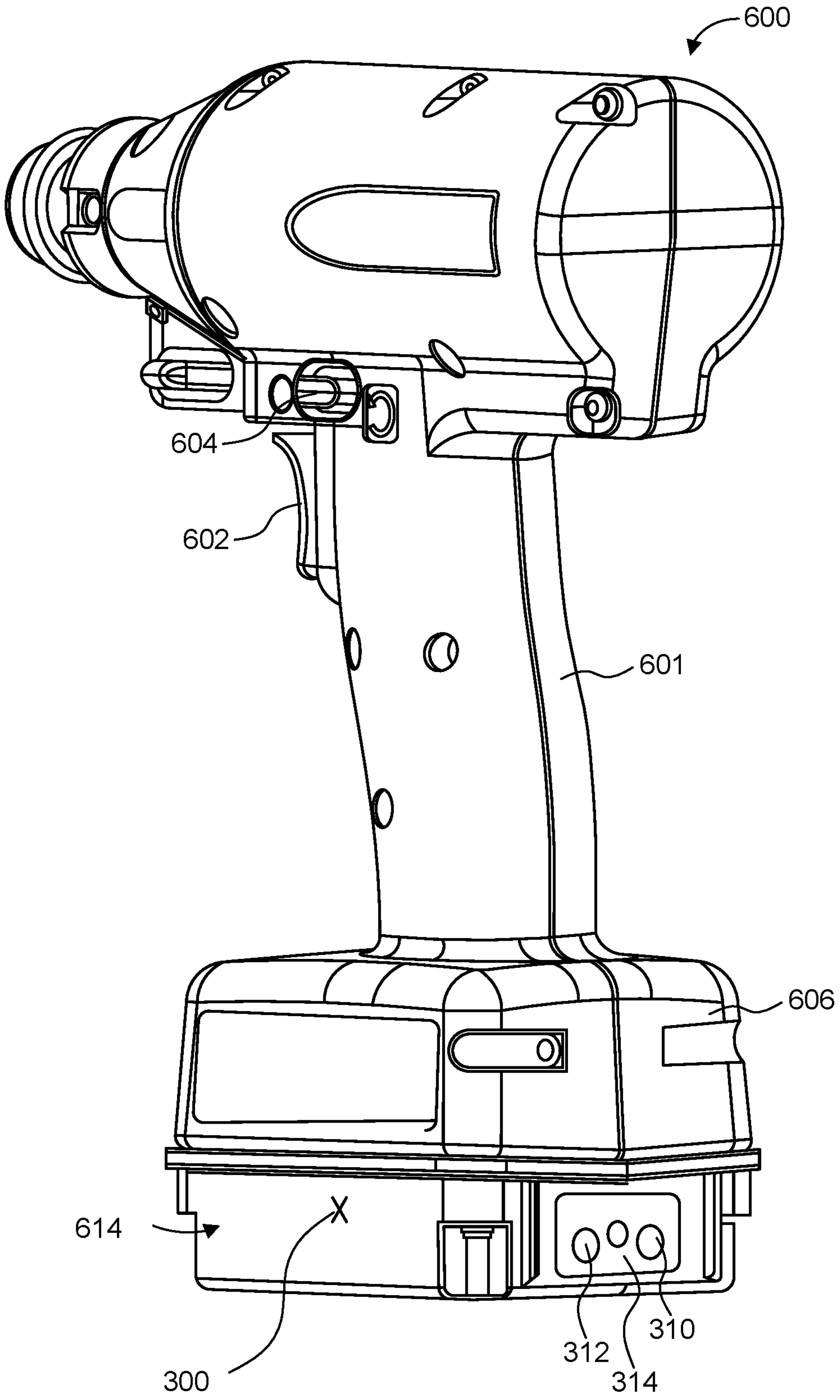
FIG. 6 is an illustration of a power tool with an external switch located on the external housing of the battery pack, as seen in FIG. 3, to wake the battery or battery pack.

FIG. 6 is an illustration of a medical power tool 600 comprising a conventional handle 601 with an external switch 312 on the battery housing to wake the attached battery or battery pack 300 (not shown in view) contained within the battery housing 606 (Upper housing)/614 (Lower housing). In the fully assembled configuration of a tool and battery or battery pack, said activation switch is configurable on the tool itself, on the battery or battery pack itself, within the tool and battery or battery pack connection circuit, or a combination of these, wherein said activation can occur by an intentional action from a user, such as pulling a trigger 602 which may also activate the drive motor, pushing a button (312) or the mere assembly of the battery or battery pack 300 into the housing 606/614 to the tool. Alternately, the battery or battery pack 300 may be configured such that a wake-up mechanism, i.e.: 230, is activated as soon as the battery is removed from its packaging, whether or not it is incorporated with the power tool, in the same overall packaging as the power tool, or if the battery or battery pack is in its own packaging. Additionally, this configuration may further comprise a status panel 314, having a status light or indicator 310 and the activation or wake-up button 312 thereon. Any configuration of these tools may also comprise a directional forward/reverse switch 604 to control the direction of the motor of the tool.

Figure 7:
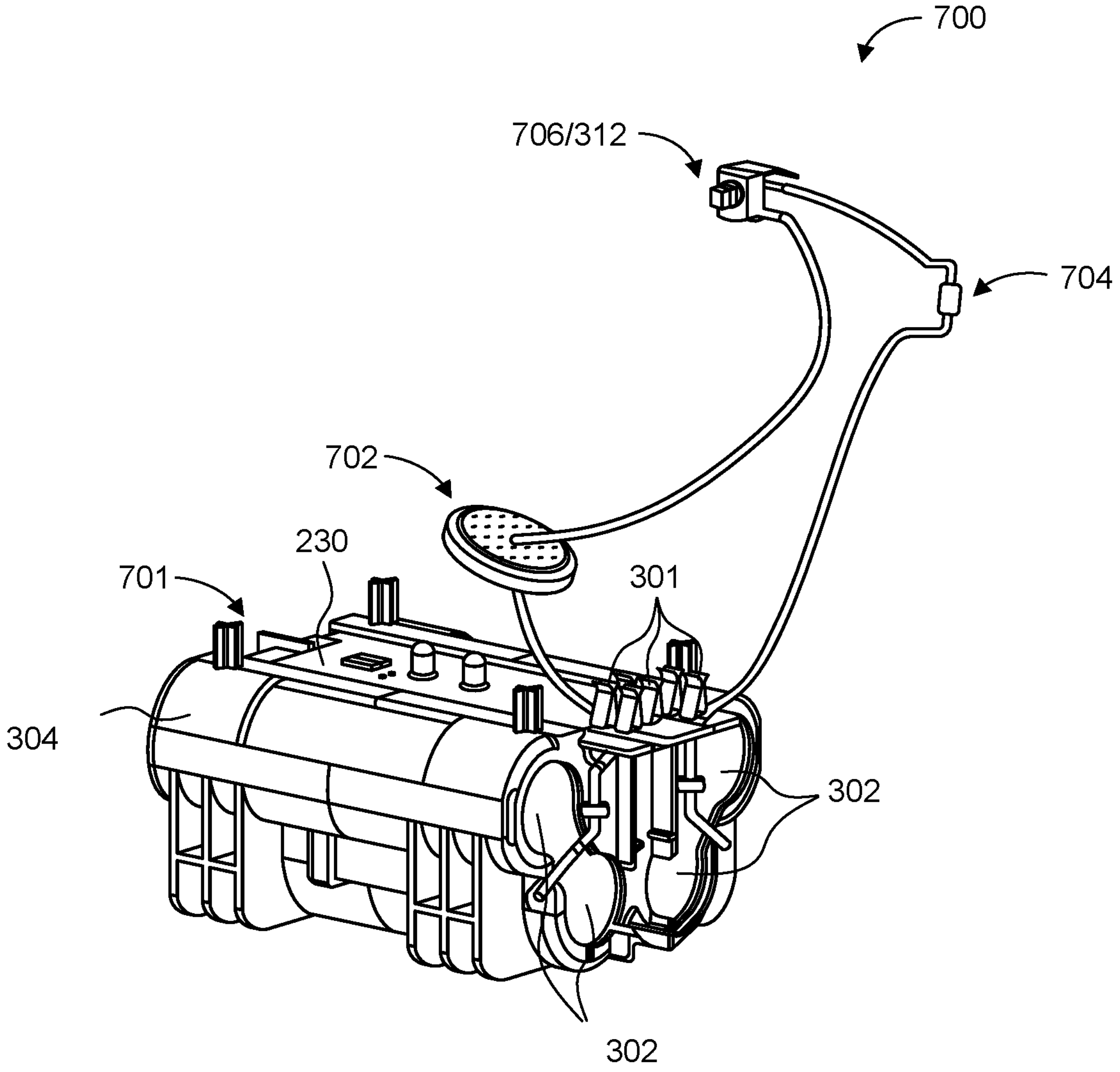
FIG. 7 is an alternate illustration of the internal battery pack as shown in FIG. 3, having a diode control circuit with a secondary battery cell configured to reactivate a hibernating medical battery, batteries, or battery pack.

As shown in FIG. 7, another embodiment of a wake-up mechanism 700 is shown illustrating a diode control 704 circuit with a secondary battery cell 702 configured to reactivate a hibernating battery, batteries or battery pack 701. In this configuration, a secondary battery cell 702 could supply the current to awaken the circuitry on the battery control board 230 following activation of a switch 706/312 or other trigger mechanism in order to fully awaken the primary battery or battery pack containing a plurality of batteries 302, sometimes nested in a battery cradle 304, and having contacts 301, as previously described. As intimated earlier, the secondary battery cell 702 configured to reactivate a hibernating battery, batteries, or battery pack 701 could be replaced by a capacitor.

Figure 8A:
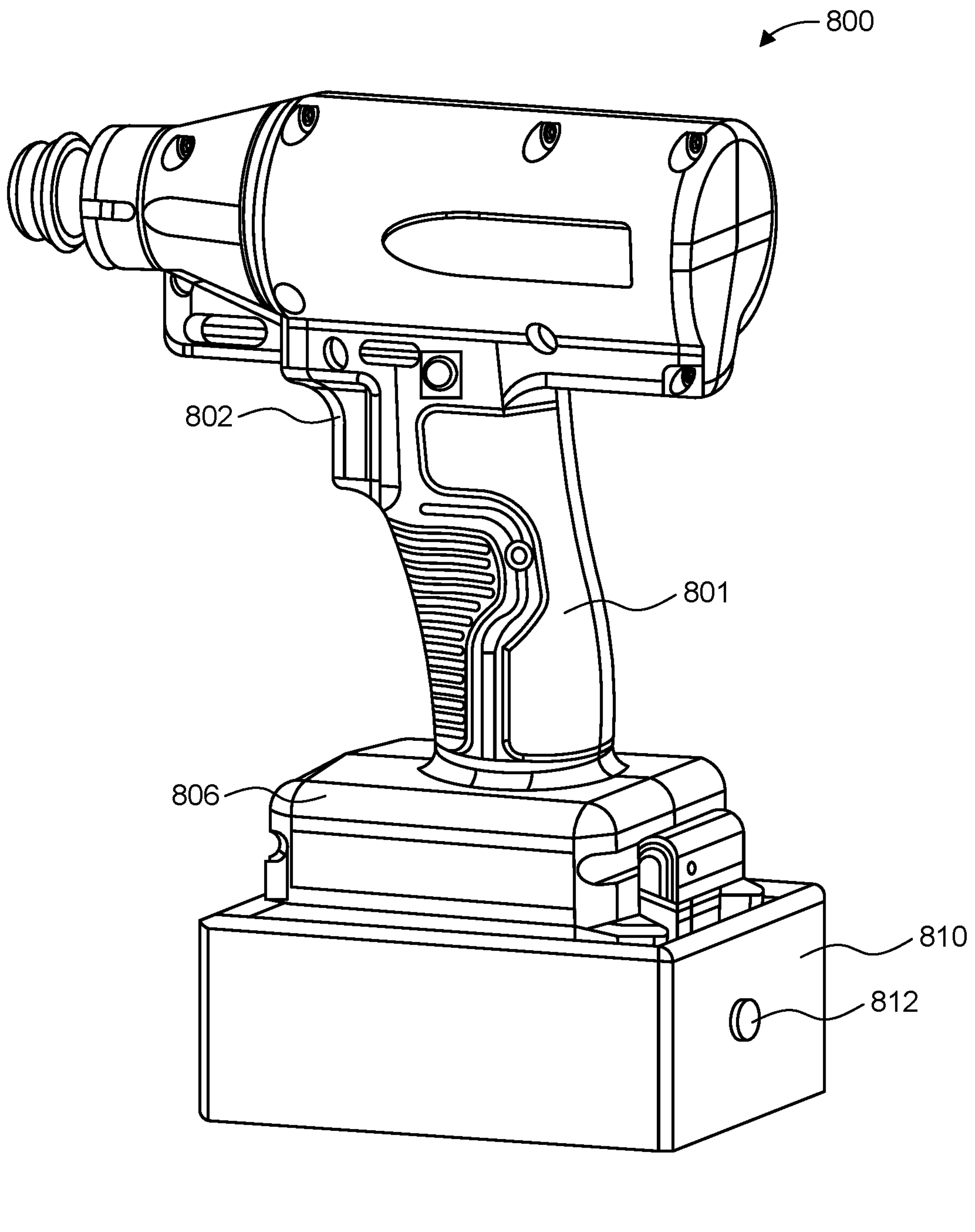
FIG. 8A is an illustration of a battery-powered power tool with a packaging component comprising a magnetic field embedded in the packaging component and covering the medical tool battery pack of the tool (in shutdown mode), capable of holding a wake activation mechanism switch in the tool or battery pack open (or closed). When the battery-powered power tool is removed from the packaging, the absence of the magnetic field provided by the packaging component allows the switch to reverse its state and activate the battery.

As shown in FIG. 8A is an illustration of a battery-powered power tool 800 with a packaging component 810 comprising a magnetic field generator component 812 embedded in the packaging component and covering the medical tool battery pack housing 806/814 of the tool (with battery pack 300—not shown) in shutdown mode) attached via a handle 801, capable of holding a wake activation mechanism switch in the tool or battery pack open (or closed). When the battery-powered power tool is removed from the packaging, the absence of the magnetic field provided by the packaging component allows the activation switch to reverse its state and activate the battery. Once activated, the battery can provide useable current to the medical device by activation of a trigger mechanism 802.

Figure 8B:
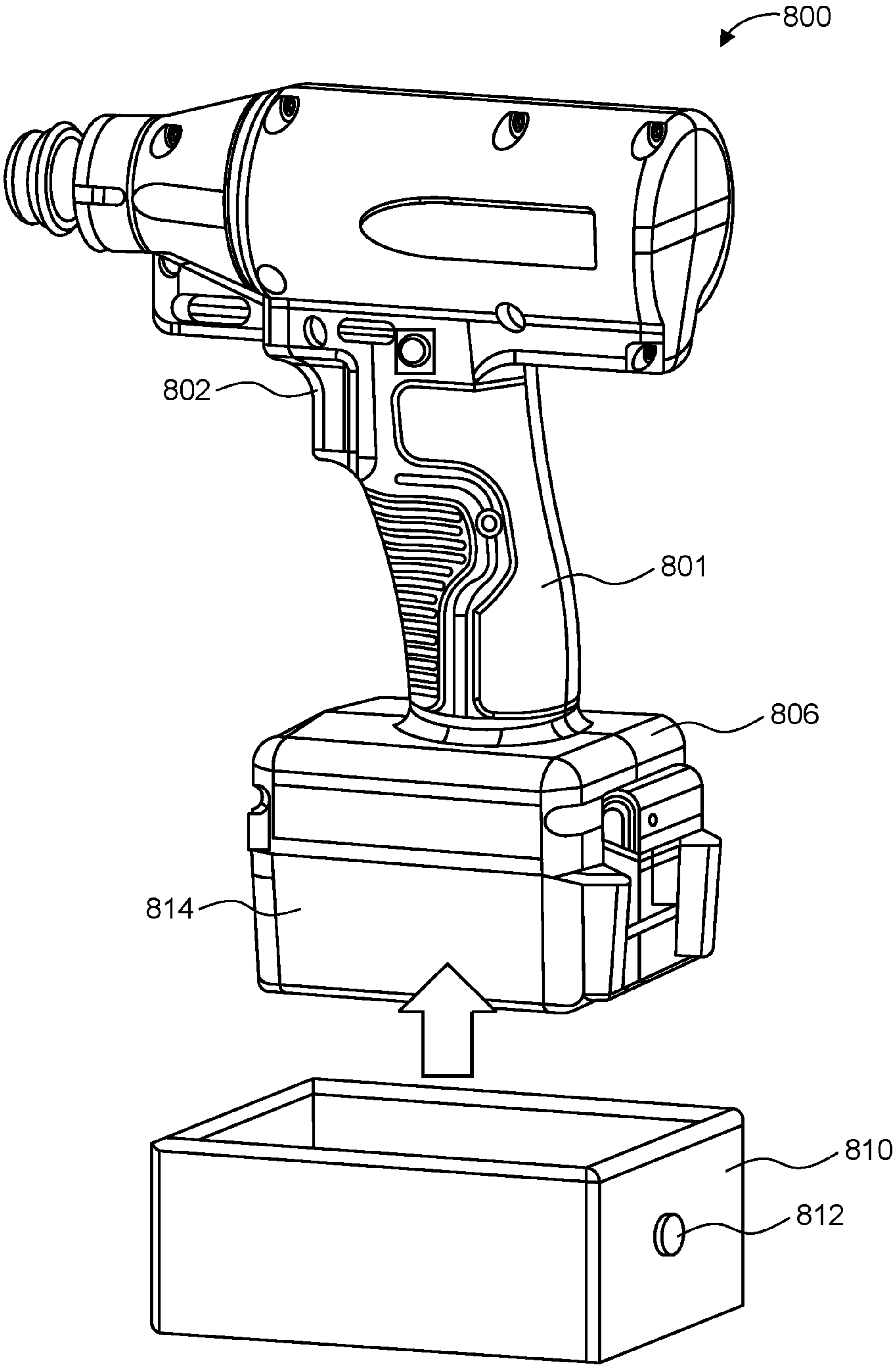
FIG. 8B is an illustration of the battery-powered power tool of FIG. 8A, removed from the packaging component, thus waking the battery from the shutdown mode, and activating a NORMAL or ACTIVE mode for the battery pack.

As shown in FIG. 8B is an illustration of the battery-powered power tool of FIG. 8A, removed from the packaging component 810 and away from the magnetic field generator component 812 embedded in the packaging component, thus waking the battery pack 300—(not shown) encased in the medical tool battery pack housing 806/814 from the shutdown mode and activating a NORMAL or ACTIVE mode for the battery pack.

Figure 9A:
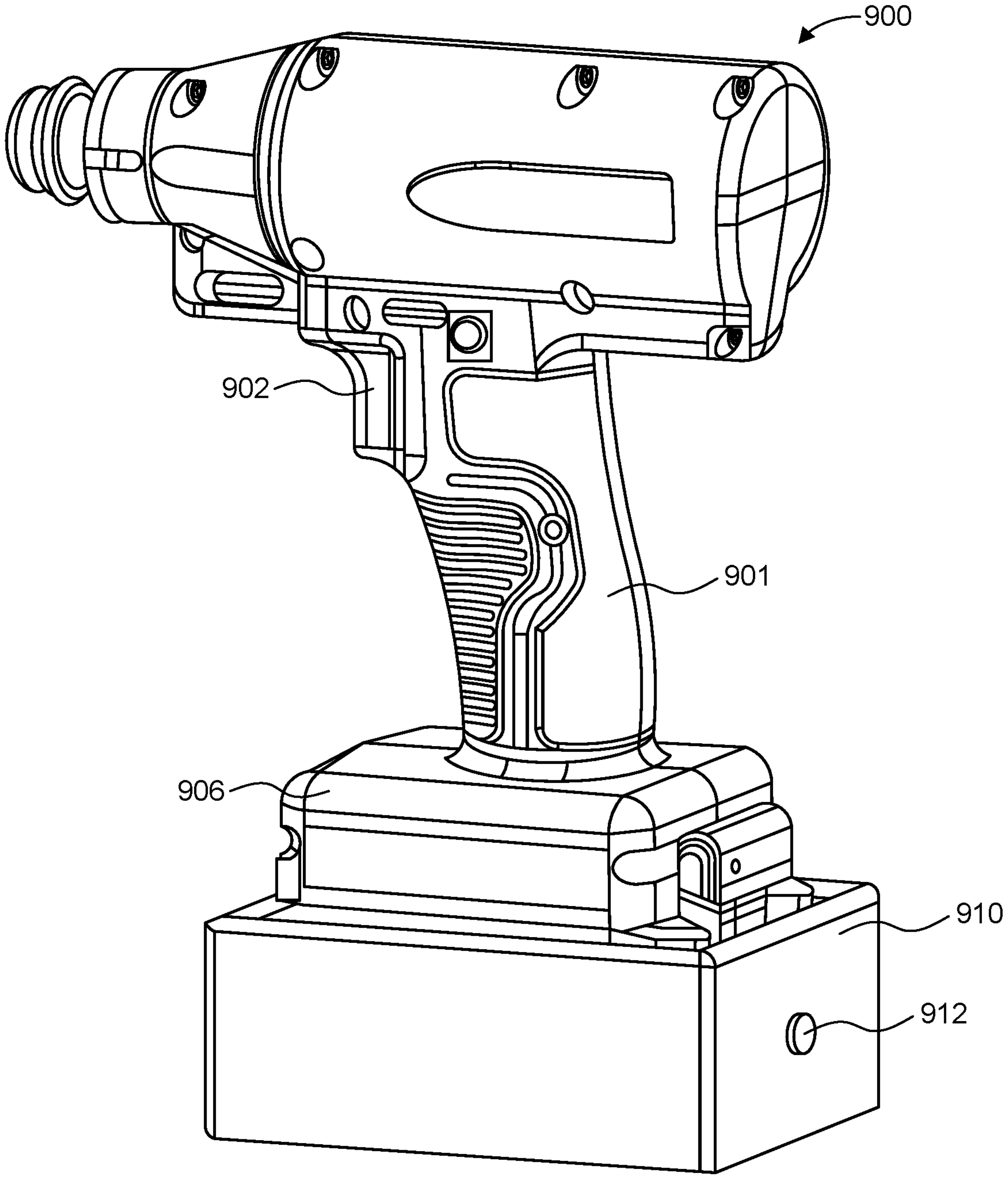
FIG. 9A is an illustration of a battery-powered power tool with a packaging component comprising an external power source, (i.e.: a battery or capacitor), electrical contacts and a switch, (i.e.: a button, a switch, or a toggle). The medical device comprising mating contacts, rests in the packaging component on the packaging electrical contacts (in shutdown mode). When the switch on the packaging component is activated by a user, a voltage is applied to the battery-powered power tool, activating the battery, and waking it from the previously shutdown state.

As shown in FIG. 9A is an illustration of a battery-powered power tool 900 with a packaging component 910 comprising an external power source 916, (i.e.: a battery or capacitor), electrical contacts 908 and a switch 912, (i.e.: a button, a switch, or a toggle). The medical device comprising mating contacts (not shown), rests in the packaging component 910 on the packaging electrical contacts 908 (with the battery pack 300) in shutdown mode). When the switch 912 on the packaging component 910 is activated by a user, a voltage is applied to the battery-powered medical tool 900, or the battery pack 300, encased in the battery housing 906/914, activating the battery and waking it from the previously shutdown state.

Figure 9B:
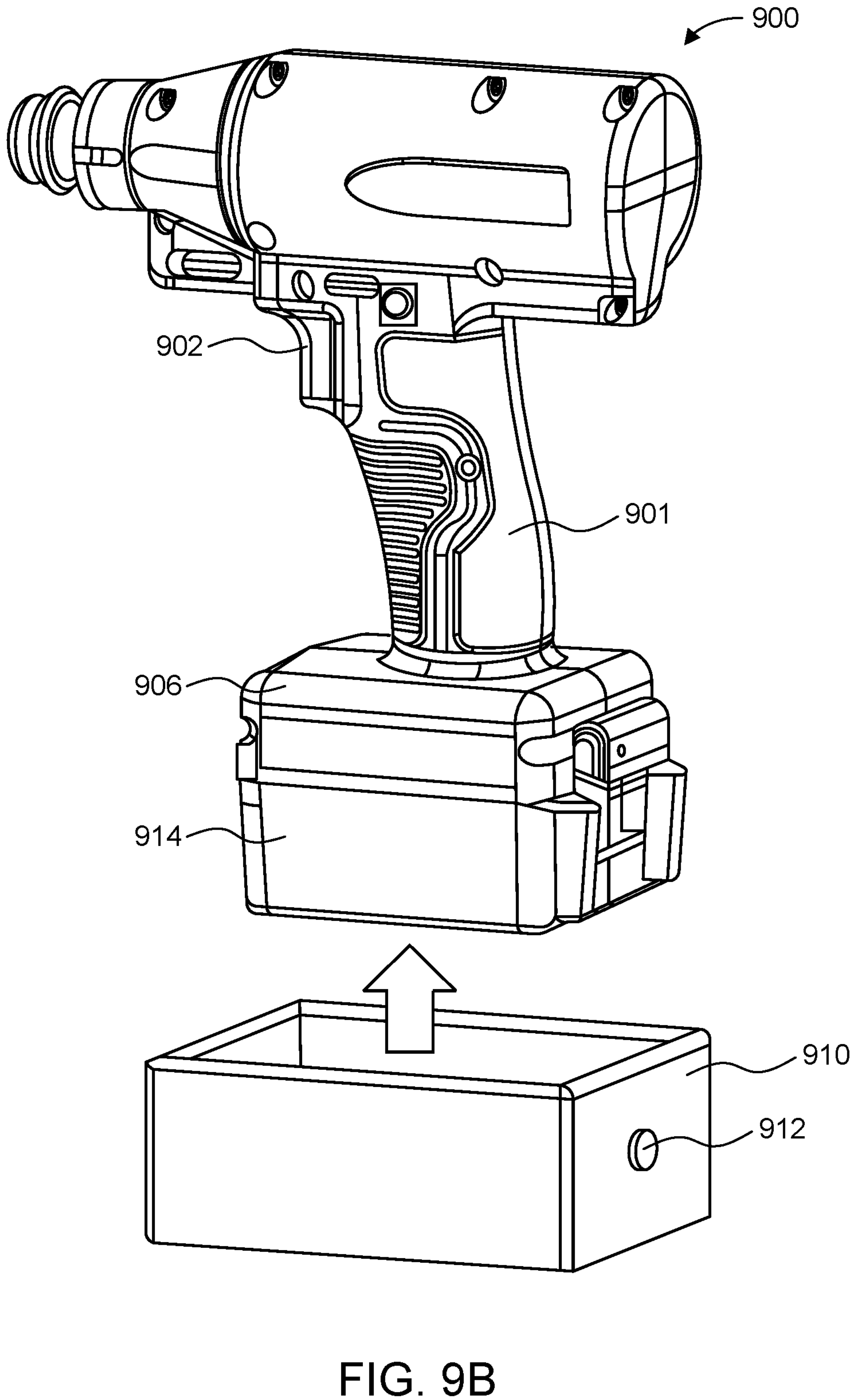
FIG. 9B is an illustration of the battery-powered power tool of FIG. 9A, removed from the packaging component after the switch has been activated and a voltage was applied to the battery-powered power tool, waking the battery pack.

As shown in FIG. 9B is an illustration of the battery-powered power tool 900 of FIG. 9A, removed from the packaging component 910 after the switch 912 has been activated and a voltage was applied to the battery-powered power medical tool or the battery pack from the external power source 916, waking the battery pack.

Figure 9C:
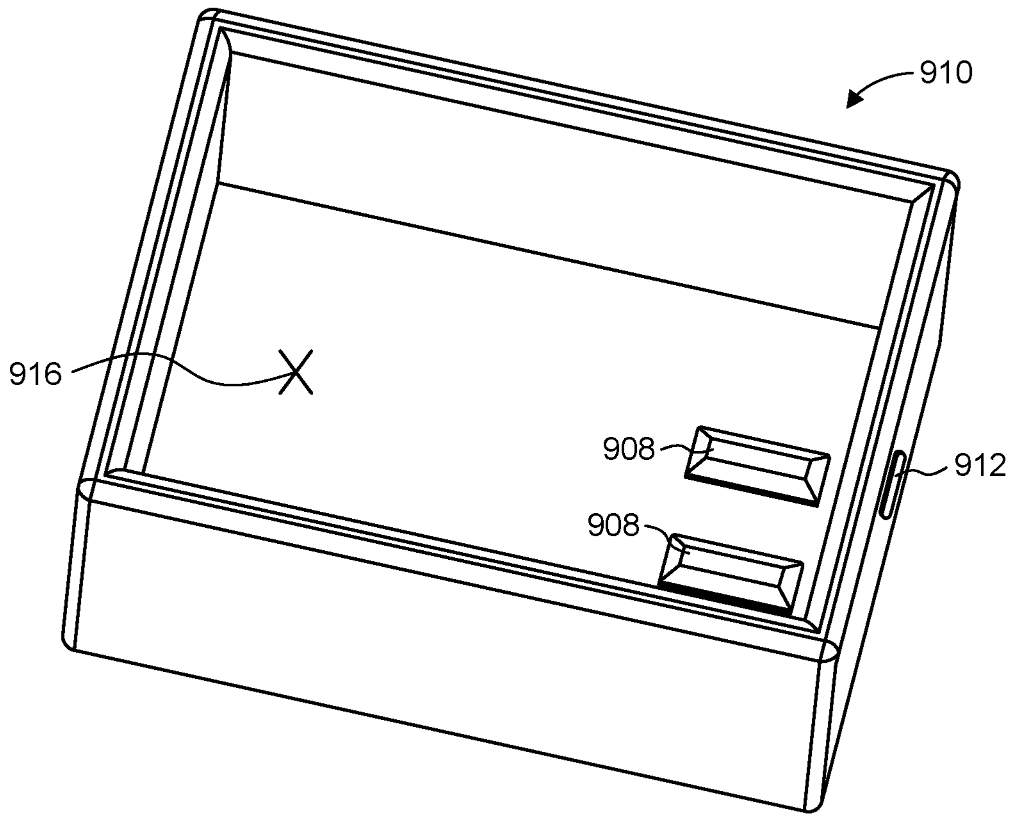
FIG. 9C is an isometric view of a packaging component as described in FIGS. 9A & 9B showing non-limiting illustrations of electrical contacts and an activation switch within the packaging. The external power source (not shown) may be contained within inner layers of the packaging, beneath or attached outside of the packaging component.

As shown in FIG. 9C is an isometric view of a packaging component 910 as described in FIGS. 9A & 9B showing non-limiting illustrations of electrical contacts 908 and an activation switch 912 within the packaging 910. The external power source 916 (not shown) may be contained within inner layers of the packaging 910, beneath or attached outside of the packaging component.

Provided here is a mechanism to wake a medical tool battery or medical battery pack from an inactive state comprising: a switch 312 on an exterior portion of a battery housing; or an electrical circuit, activated by a trigger mechanism 100; or a pre-programmed timing event mechanism incorporated within circuitry 230 of the medical battery or medical battery pack 300; an integrated secondary cell, a battery, batteries 302, or other power supply; or a primary cell; or an external charger, batteries, or other power supply; or an integrated capacitor comprising 702: i. a timed circuit breakage via inline fuse; ii. a timed circuit breakage via transistor; or iii. a circuit breakage via mechanical means; wherein the circuit closure is either permanent or momentary or a wireless activation mechanism; or an electromagnetic field mechanism; or a magnetic field mechanism 410; or a combination thereof, wherein said medical tool battery or medical battery pack comprises a medical grade 302 battery that has been placed in an inactive state to preserve a battery or battery pack charge or minimize a power loss until an on-demand power level for the medical battery or medical battery pack is activated by an end user.

In some embodiments of the mechanism, an inactive state comprises: a SLEEP mode; or a LOW POWER mode; or a SHUTDOWN mode; or an ULTRA-LOW POWER mode; or a combination thereof.

In some embodiments of the mechanism, said medical tool battery or medical battery pack 300 is provided integral with a sterile medical tool 400, 500, 600 to an end user.

In some embodiments of the mechanism, said integral medical tool battery 302 or medical battery pack 300 is rechargeable.

In some embodiments of the mechanism, said integral medical tool battery 302 or medical battery pack 300 is disposable.

In some embodiments of the mechanism, said medical tool battery 302 or medical battery pack 300 is provided separately from a sterile surgical power tool to an end user.

In some embodiments of the mechanism, said separately provided medical tool battery 302 or medical battery pack 300 is provided in a sterile state.

In some embodiments of the mechanism, said separately provided medical tool battery 302 or medical battery pack 300 is provided in a non-sterile state.

In some embodiments of the mechanism, said separately provided medical tool battery 302 or medical battery pack 300 is rechargeable.

In some embodiments of the mechanism, said separately provided medical tool battery 302 or medical battery pack 300 is disposable.

In some embodiments, the mechanism further comprises a visual indicator 310 to alert an end user about the medical tool battery 302 or medical battery pack 300 status.

In some embodiments, the mechanism further comprises an audible indicator (not shown) to alert an end user about the medical tool battery or medical battery pack status.

In some embodiments of the mechanism, said medical tool battery 302 or medical battery pack 300 is rechargeable via an external cord attachment.

In some embodiments of the mechanism, said medical tool battery 302 or medical battery pack 300 is rechargeable via a wireless charging coil.

In some embodiments of the mechanism, said mechanism is configured for a reusable medical tool battery 302 or medical battery pack 300.

In some embodiments of the mechanism, said mechanism is configured for a limited-use medical tool battery 302 or medical battery pack 300.

In some embodiments of the mechanism, said mechanism is configured for a single-use medical tool battery 302 or medical battery pack 300.

In some embodiments of the mechanism, said mechanism is configured for use with a pre-packaged sterile, reusable, limited use, or single-use medical device battery 302 or medical battery pack 300.

Provided herein is a battery-powered medical device 400, 500, 600 having a mechanism to wake a medical grade battery or medical grade battery pack from an inactive state comprising: an activation switch 312. 410 either internally or on an exterior portion of the medical device 400, 500, 600, 700; or a switch 312 on an exterior portion of a battery or battery pack housing 300, 406/414, 606/614; or an electrical circuit, activated by a trigger mechanism 100, 412, 602; or a pre-programmed timing event mechanism incorporated within the circuitry 230 of the medical device; or a pre-programmed timing event mechanism incorporated within the circuitry 230 of said medical grade battery or medical grade battery pack 300; an integrated secondary cell 702, a battery 302, batteries 302, or other power supply; or a primary cell; or an external charger, batteries, or other power supply; or an integrated capacitor comprising 702: i. a timed circuit breakage via inline fuse; ii. a timed circuit breakage via transistor; or iii. a circuit breakage via mechanical means; wherein the circuit closure is either permanent or momentary or a wireless activation mechanism; or an electromagnetic field mechanism; or a magnetic field mechanism 410, 420, 530 or a combination thereof; wherein said medical grade battery or medical grade battery pack had been placed in an inactive state to preserve a battery charge until the wake mechanism 230 is activated.

In some embodiments, said battery-powered medical device is provided to an end user in a sealed, sterile package.

In some embodiments, said battery-powered medical device further comprises an integrated medical grade battery 302 or medical grade battery pack 300.

In some embodiments, said battery-powered medical device is delivered to an end user without an integrated medical grade battery 302 or medical grade battery pack 300.

In some embodiments of said battery-powered medical device, said non-integrated medical grade battery 302 or medical grade battery pack 300 is provided sterile, and separated from the battery-powered medical device in a second sealed, sterile package, either in or out of the battery-powered medical device sealed, sterile package.

In some embodiments of said battery-powered medical device, said non-integrated medical grade battery 302 or medical grade battery pack 300 is provided non-sterile, and separately from the medical device.

In some embodiments of said battery-powered medical device, said battery-powered medical device is a reusable power tool.

In some embodiments of said battery-powered medical device, said battery-powered medical device is a limited-use power tool.

In some embodiments of said battery-powered medical device, said battery-powered medical device is a single-use power tool.

In some embodiments of said battery-powered medical device, said medical grade battery 302 or medical grade battery pack 300 inactive state comprises: a SLEEP mode; or a LOW POWER mode; or a SHUTDOWN mode; or an ULTRA-LOW POWER mode; or a combination thereof.

In some embodiments of said battery-powered medical device wherein said device is provided to an end user in a sealed, sterile package comprising an integrated battery, said medical grade battery 302 or medical grade battery pack 300 is rechargeable.

In some embodiments of said battery-powered medical device wherein said device is provided to an end user without an integrated medical grade battery 302 or medical grade battery pack 300, said medical grade battery or medical grade battery pack is rechargeable.

In some embodiments of said battery-powered medical device wherein said device is provided to an end user in a sealed, sterile package comprising an integrated medical grade battery 302 or medical grade battery pack 300, said medical grade battery or medical grade battery pack is disposable.

In some embodiments of said battery-powered medical device wherein said device is provided to an end user without an integrated medical grade battery 302 or medical grade battery pack 300, said medical grade battery or medical grade battery pack is disposable.

Some embodiments of said battery-powered medical device further comprise a visual indicator 312 to alert an end user about the battery status.

Some embodiments of said battery-powered medical device further comprise an audible indicator (not shown) to alert an end user about the battery status.

In some embodiments of said battery-powered medical device wherein said device is provided to an end user with an integrated medical grade battery 302 or medical grade battery pack 300, said medical grade battery or medical grade battery pack is rechargeable via an external cord attachment.

In some embodiments of said battery-powered medical device wherein said device is provided to an end user without an integrated medical grade battery 302 or medical grade battery pack 300, said medical grade battery or medical grade battery pack is rechargeable via an external cord attachment.

In some embodiments of said battery-powered medical device wherein said device is provided to an end user with an integrated medical grade battery 302 or medical grade battery pack 300, said device is provided to an end user in a sealed, sterile package comprising an integrated medical grade battery or medical grade battery pack wherein said medical grade battery or medical grade battery pack is rechargeable via a wireless charging coil.

In some embodiments of said battery-powered medical device wherein said device is provided to an end user without an integrated medical grade battery 302 or medical grade battery pack 300, said medical grade battery is rechargeable via a wireless charging coil.

In some embodiments of said battery-powered medical device, said medical grade battery-powered medical device comprises: a sterile surgical power drill; a sterile surgical power reamer; a sterile surgical power saw; a sterile dissection power tool; a sterile impaction power tool; a sterile retraction power tool; a sterile laparoscopic power tool; a sterile endoscopic power tool; a sterile stapling power tool; a sterile endoscopic power resection tool; a cautery tool; or a sterile head lamp.

Provided herein is a medical power tool 400, 500, 600 comprising an integrated medical grade battery 302 or medical grade battery pack 300 previously placed in an inactive state; wherein said medical power tool comprises a wake mechanism 100, 230, 312, 402, 404, 410, 412, 420, 530, 602 700 configured to switch the medical grade battery 300, 302 from an inactive state to an active mode, said wake mechanism comprising: a switch 312, 402, 404, 412, 420, 602; on an exterior portion of the power tool; or an electrical circuit 230, activated by a trigger 100, 412, 602; or a pre-programmed timing event mechanism incorporated within the circuitry of the tool 200, 230, 412, 602; or a pre-programmed timing event mechanism incorporated within the circuitry of the battery 230, 700; or a wireless activation mechanism; or an electromagnetic field mechanism; or a magnetic field mechanism 402, 403, 404, 405, 408, 410, 420, 530; or a combination thereof, wherein said medical grade battery 302 or medical grade battery pack 300 had been placed in an inactive state to preserve a battery charge until the wake mechanism is activated.

In some embodiments of said medical power tool comprising an integrated medical grade battery or battery pack previously placed in an inactive state, said medical power tool is provided to an end user in a sealed, sterile package.

In some embodiments of said medical power tool comprising an integrated medical grade battery or battery pack previously placed in an inactive state, said medical power tool is a reusable power tool.

In some embodiments of said medical power tool comprising an integrated medical grade battery or battery pack previously placed in an inactive state, said medical power tool is a limited-use power tool.

In some embodiments of said medical power tool comprising an integrated medical grade battery or battery pack previously placed in an inactive state, said medical power tool is a single-use power tool.

In some embodiments of said medical power tool comprising an integrated medical grade battery or battery pack previously placed in an inactive state, said battery inactive state comprises a SLEEP mode; or a LOW POWER mode; or a SHUTDOWN mode; or an ULTRA-LOW POWER mode; or a combination thereof.

In some embodiments of said medical power tool comprising an integrated medical grade battery or battery pack previously placed in an inactive state, said reusable power tool provided to an end user in a sealed, sterile package comprises a sterile surgical power drill; a sterile surgical power reamer; sterile surgical power saw; a sterile dissection power tool; a sterile impaction power tool; a sterile retraction power tool; a sterile laparoscopic power tool; a sterile endoscopic power tool; a sterile stapling power tool; a sterile endoscopic power resection tool; a cautery tool; or a sterile head lamp.

In some embodiments of said medical power tool comprising an integrated medical grade battery or battery pack previously placed in an inactive state, said medical grade battery or battery pack wake mechanism is activated from its inactive state when removed from the sealed, sterile package.

In some embodiments of said medical power tool comprising an integrated medical grade battery or battery pack previously placed in an inactive state, said medical grade battery or battery pack is awakened from its inactive state when the wake mechanism is activated by the end user at the time of use.

Provided herein is a surgical power tool comprising: a non-integrated medical grade battery or battery pack previously placed in an inactive state wherein said surgical power tool 400, 500, 600 comprises a wake mechanism 230, 312, 402, 404, 410, 420, 530, 700 configured to switch the battery from an inactive state to an active mode, said wake mechanism comprising: a switch on an exterior portion of the power tool 706, 312 or handle 401; or an electrical circuit 230, activated by a trigger mechanism 100; or a pre-programmed timing event mechanism incorporated within the circuitry of the tool; or a wireless activation mechanism; or an electromagnetic field mechanism; or a magnetic field mechanism 420, 530; or a combination thereof, wherein said non-integrated medical grade battery had been placed in an inactive state to preserve a battery charge until placed in the surgical power tool and awakened by the surgical power tool wake mechanism.

In some embodiments of said surgical power tool comprising a non-integrated medical grade battery or battery pack previously placed in an inactive state, said non-integrated medical grade battery further comprises a pre-programmed timing event mechanism incorporated within the circuitry of the battery; or a wireless activation mechanism; or an electromagnetic field mechanism; or a magnetic field mechanism; or a combination thereof, wherein said medical grade battery had been placed in an inactive state to preserve a battery charge until activated by the battery activation mechanism.

In some embodiments of said surgical power tool comprising a non-integrated medical grade battery or battery pack previously placed in an inactive state, said surgical power tool is provided to an end user in a sealed, sterile package.

In some embodiments of said surgical power tool comprising a non-integrated medical grade battery or battery pack previously placed in an inactive state, said non-integrated medical grade battery is provided sterile, and separated from the surgical power tool, in the medical device's sealed, sterile package.

In some embodiments of said surgical power tool comprising a non-integrated medical grade battery or battery pack previously placed in an inactive state, said non-integrated medical grade battery is provided non-sterile, separate from the surgical power tool, and not in the medical device's sealed, sterile package.

In some embodiments of said surgical power tool comprising a non-integrated medical grade battery or battery pack previously placed in an inactive state, said surgical power tool is a reusable power tool.

In some embodiments of said surgical power tool comprising a non-integrated medical grade battery or battery pack previously placed in an inactive state, said surgical power tool is a limited-use power tool.

In some embodiments of said surgical power tool comprising a non-integrated medical grade battery or battery pack previously placed in an inactive state, said surgical power tool is a single-use power tool.

In some embodiments of said surgical power tool comprising a non-integrated medical grade battery or battery pack previously placed in an inactive state, said medical grade battery inactive state comprises: a SLEEP mode; or a LOW POWER mode; or a SHUTDOWN mode; or an ULTRA-LOW POWER mode; or a combination thereof.

In some embodiments of said surgical power tool comprising a non-integrated medical grade battery or battery pack previously placed in an inactive state, said surgical power tool comprises a sterile surgical power drill; a sterile surgical power reamer; a sterile surgical power saw; a sterile dissection power tool; a sterile impaction power tool; a sterile retraction power tool; a sterile laparoscopic power tool; a sterile endoscopic power tool; a sterile stapling power tool; a cautery tool; or a sterile endoscopic power resection tool.

In any embodiment of the wake mechanism comprising an activation mechanism, said activation mechanism is configured with a momentary activation mode; or a permanent activation mode.

In any embodiment of the wake mechanism comprising an activation mechanism, said activation mechanism is configured to reactivate hibernating batteries integrated into medical devices using a circuit closure mechanism activated by: a trigger 100, 101, 412, 602, embedded switch 410, contact, or similar mechanism; or an exterior accessed button 312, switch, or similar mechanism; or an external magnetic contact 402, 404; or an external key or pin; wherein the waking voltage is supplied by: an integrated secondary cell 702, a battery 302, batteries 300, or other power supply; or a primary cell; or an external charger, batteries, or other power supply; or an integrated capacitor 702 comprising: i. a timed circuit breakage via inline fuse; ii. a timed circuit breakage via transistor; or iii. a circuit breakage via mechanical means; wherein the circuit closure is either permanent or momentary.

In any embodiment of the wake mechanism comprising an activation mechanism, said activation mechanism may be configured to subsequently reverse the activation process and deactivate a previously activated battery and return it to its hibernating state.

Provided herein is a medical device battery or battery pack 700 comprising a medical grade battery 302 or battery pack 300 previously placed in an inactive state; wherein said medical grade battery or battery pack comprises a wake mechanism, 308 configured to switch the medical grade battery or battery pack from an inactive state to an active mode, said wake mechanism comprising a switch 706 on an exterior portion of the medical grade battery or battery pack; or a switch on an exterior portion of a battery housing containing said battery or battery pack 312; or an interior electrical circuit 200, 230, activated by a trigger 100, 101, 412, 602 exterior to said medical grade battery or battery pack; or an external electrical circuit, activated by a trigger 100, 101, 412, 602, exterior to said medical grade battery or battery pack; or a pre-programmed timing event mechanism incorporated within the circuitry of the medical grade battery or battery pack; or a pre-programmed timing event mechanism incorporated within the circuitry of a tool using said medical grade battery or battery pack; or a wireless activation mechanism; or an electromagnetic field mechanism; or a magnetic field mechanism 420, 530; or a combination thereof, wherein said medical grade battery or battery pack had been placed in an inactive state to preserve a battery charge until the wake mechanism is activated.

In some embodiments of the medical grade battery or battery pack comprising a medical grade battery or battery pack previously placed in an inactive state, wherein said medical grade battery or battery pack is provided to an end user in a sealed, sterile package.

In some embodiments of the medical grade battery or battery pack, said medical grade battery or battery pack is configured for use in a reusable medical power tool.

In some embodiments of the medical grade battery or battery pack comprising a medical grade battery or battery pack previously placed in an inactive state, wherein said medical grade battery or battery pack is configured for use in a limited-use medical power tool.

In some embodiments of the medical grade battery or battery pack comprising a medical grade battery or battery pack previously placed in an inactive state, wherein said medical grade battery or battery pack is configured for use in a single-use medical power tool.

In some embodiments of the medical grade battery or battery pack comprising a medical grade battery or battery pack previously placed in an inactive state, wherein said medical grade battery or battery pack comprises a NORMAL active mode and an inactive state which comprises: a SLEEP mode; or a LOW POWER mode; or a SHUTDOWN mode; or an ULTRA-LOW POWER; or a combination thereof.

In some embodiments of the medical grade battery or battery pack comprising a medical grade battery or battery pack previously placed in an inactive state, wherein said medical grade battery or battery pack is configured for use in a sterile surgical power drill; a sterile surgical power reamer; a sterile surgical power saw; a sterile dissection power tool; a sterile impaction power tool; a sterile retraction power tool; a sterile laparoscopic power tool; a sterile endoscopic power tool; a sterile stapling power tool; a sterile endoscopic power resection tool; a cautery tool; or a sterile head lamp.

In some embodiments of the medical grade battery or battery pack comprising a medical grade battery or battery pack previously placed in an inactive state, wherein said medical grade battery or battery pack is provided to an end user in a sealed, sterile package, and wherein said medical grade battery or battery pack wake mechanism is awakened from its inactive state when removed from the sealed, sterile package.

In some embodiments of the medical grade battery or battery pack comprising a medical grade battery or battery pack previously placed in an inactive state, said medical grade battery or battery pack is awakened from its inactive state when the wake mechanism is activated by the end user at the time of use.

Provided herein is a transitionable medical-grade battery or battery pack 300 for a battery-powered medical device comprising: a medical grade battery or battery pack capable of being transitioned between an inactive state and an active state; wherein said medical grade battery or battery pack or said battery-powered medical device 800 comprises a wake mechanism configured to switch the medical grade battery from an inactive state to an active mode or returning it to an inactive state, said wake mechanism comprising: a switch 312 on an exterior portion of the medical grade battery or battery pack; or a switch on an exterior portion of a battery housing containing said battery or battery pack; or an interior electrical circuit, activated by a trigger exterior to said medical grade battery or battery pack; or an external electrical circuit 230, activated by a trigger exterior to said medical grade battery or battery pack; an internal switch or electrical circuit within the battery-operated medical device 308, activated by a magnetic field mechanism exterior to said battery-operated medical device 810, or a pre-programmed timing event mechanism incorporated within the circuitry of the medical grade battery or battery pack; or a pre-programmed timing event mechanism incorporated within the circuitry of a tool using said medical grade battery or battery pack; or a wireless activation mechanism; or an electromagnetic field mechanism; or a magnetic field mechanism; or a combination thereof, wherein said transitionable medical grade battery or battery pack is configurable to be placed in an inactive state to preserve a battery charge until the wake mechanism is activated and brings the medical grade battery or battery pack into an active state; or wherein said transitionable medical grade battery or battery pack is configurable to be switched from an active state capable of discharging useful current to operate a battery-powered medical device a battery charge until the wake mechanism is deactivated and brings the medical grade battery or battery pack back to an inactive state.

In some embodiments of the transitionable medical-grade battery or battery pack for a battery-powered medical device, said wake mechanism is activated by a magnetic field component 812 embedded within packaging 810 configured to hold or transport said medical grade battery or battery pack or said battery-powered medical device.

In some embodiments of the transitionable medical-grade battery or battery pack for a battery-powered medical device, said medical grade battery or battery pack is provided to an end user in a sealed, sterile package.

In some embodiments of the transitionable medical-grade battery or battery pack for a battery-powered medical device, said medical grade battery or battery pack is configured for use in a reusable medical power tool.

In some embodiments of the transitionable medical-grade battery or battery pack for a battery-powered medical device, said medical grade battery or battery pack is configured for use in a limited-use medical power tool.

In some embodiments of the transitionable medical-grade battery or battery pack for a battery-powered medical device, said medical grade battery or battery pack is configured for use in a single-use medical power tool.

In some embodiments of the transitionable medical-grade battery or battery pack for a battery-powered medical device, said medical grade battery or battery pack is configured for use in a single-use medical power tool.

In some embodiments of the transitionable medical-grade battery or battery pack for a battery-powered medical device, said medical grade battery or battery pack comprises a NORMAL active mode and an inactive state which comprises: a SLEEP mode; or a LOW POWER mode; or a SHUTDOWN mode; or an ULTRA-LOW POWER; or a combination thereof.

In some embodiments of the transitionable medical-grade battery or battery pack for a battery-powered medical device, said medical grade battery or battery pack is configured for use in: a sterile surgical power drill; a sterile surgical power reamer; a sterile surgical power saw; a sterile dissection power tool; a sterile impaction power tool; a sterile retraction power tool; a sterile laparoscopic power tool; a sterile endoscopic power tool; a sterile stapling power tool; a sterile endoscopic power resection tool; a cautery tool; or a sterile headlamp.

In some embodiments of the transitionable medical-grade battery or battery pack for a battery-powered medical device, said medical grade battery or battery pack wake mechanism is awakened from its inactive state when removed from the sealed, sterile package.

In some embodiments of the transitionable medical-grade battery or battery pack for a battery-powered medical device, said medical grade battery or battery pack is awakened from its inactive state when the wake mechanism is activated by the end user at the time of use.

Provided herein is a battery-powered medical device having a mechanism to wake a medical grade battery or medical grade battery pack from an inactive state comprising: a packaging component configurable to hold an activation switch in an open position while in contact with the battery-powered medical device, the medical grade battery or medical grade battery pack; wherein said medical grade battery or medical grade battery pack had been previously placed in an inactive or shutdown state.

In some embodiments of the battery-powered medical device having a mechanism to wake a medical grade battery or medical grade battery pack from an inactive state, the magnetic field mechanism comprises a permanent magnet; or an electromagnet; or a temporary battery.

Provided herein is a battery-powered medical device having a mechanism to wake a medical grade battery or medical grade battery pack from an inactive state comprising: a packaging component comprising: a power source; packaging electrical contacts; and a switch; wherein said battery-powered medical device comprises: mating medical device electrical contacts configurable to mate with the packaging component electrical contacts; and wherein the medical device electrical contacts rest upon the packaging electrical contacts within the packaging component, and wherein when said switch is activated by an end-user, a voltage is applied to the medical device or medical grade battery or medical grade battery pack, activating said medical grade battery or medical grade battery pack from a previously shut down state.

In some embodiments, of the battery-powered medical device having a mechanism to wake a medical grade battery or medical grade battery pack from an inactive state comprising a packaging component wherein, when said battery-powered medical device with the mating medical device electrical contacts is replaced in said packaging component with the mating packaging electrical contacts, said medical grade battery or medical grade battery pack is deactivated and returned to an inactive state.

Provided herein is a battery-powered medical device having a mechanism to wake a medical grade battery or medical grade battery pack from an inactive state comprising: a packaging component comprising a magnetic field mechanism capable of holding an activation switch in an open position while in contact with the battery-powered medical device, the medical grade battery or medical grade battery pack; wherein said medical grade battery or medical grade battery pack had been previously placed in an inactive or shutdown state.

In some embodiments of the battery-powered medical device having a mechanism to wake a medical grade battery or medical grade battery pack from an inactive state, the magnetic field mechanism comprises a permanent magnet; or an electromagnet; or a temporary battery.

In some embodiments of the battery-powered medical device having a mechanism to wake a medical grade battery or medical grade battery pack, when said battery-powered medical device with the mating medical device is replaced in said packaging component with the magnetic field mechanism, said medical grade battery or medical grade battery pack is deactivated and returned to an inactive state.

Provided herein is a battery-powered medical device having a mechanism to wake a medical grade battery or medical grade battery pack from an inactive state comprising: a packaging component comprising: a power source; packaging electrical contacts; and a switch; wherein said battery-powered medical device comprises: mating medical device electrical contacts configurable to mate with the packaging component electrical contacts; and wherein the medical device electrical contacts rest upon the packaging electrical contacts within the packaging component, and wherein when said switch is activated by an end-user, a voltage is applied to the medical device or medical grade battery or medical grade battery pack, activating said medical grade battery or medical grade battery pack from a previously shut down state.

In some embodiments, of the battery-powered medical device having a mechanism to wake a medical grade battery or medical grade battery pack from an inactive state comprising a packaging component wherein, when said battery-powered medical device with the mating medical device electrical contacts is replaced in said packaging component with the mating packaging electrical contacts, said medical grade battery or medical grade battery pack is deactivated and returned to an inactive state.

Provided herein is a medical device packaging component containing a magnetic field mechanism capable of holding a switch open or closed, as in FIG. 4B. When the medical device is removed from the packaging, the absence of the magnetic field allows for the switch to reverse its state and activate the battery from a previously shutdown state.

In some embodiments, when said battery-powered medical device with the mating medical device electrical contacts is replaced in said packaging component with the mating packaging electrical contacts, said medical grade battery or medical grade battery pack is deactivated and returned to an inactive state.

Provided herein is a medical device packaging component containing an external power source (i.e., battery), contacts, and a switch (i.e., button switch, toggle). The medical device, with mating contacts, rests in the packaging on the packaging contacts. When the switch on the packaging is activated, a voltage is applied to the medical device, activating the battery from a previously shutdown state.

In some embodiments, when said battery-powered medical device with the mating medical device electrical contacts is replaced in said packaging component with the mating packaging electrical contacts, said medical grade battery or medical grade battery pack is deactivated and returned to an inactive state.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A medical power tool system comprising:

at least one battery in an inactive state;

a sterile medical power tool including a sterile exterior housing;

a sealed sterile package that includes the at least one battery and the medical power tool;

a wake mechanism coupled to the medical power tool and configured to switch the at least one battery from an inactive state to an active mode in response to a waking voltage supplied by at least one of an external charger, an external at least one battery, or combinations thereof;

wherein the at least one battery is in the inactive state to preserve a battery charge until the wake mechanism is activated.

2. The medical power tool system of claim 1, wherein said medical power tool is a limited-use power tool.

3. The medical power tool system of claim 1 comprising a discharge (DSG) field-effect transistor (FET), wherein the battery inactive state comprises:

an ULTRA-LOW POWER mode where the DSG FET is off.

4. The medical power tool system of claim 3, wherein the medical power tool comprises a sterile surgical power drill.

5. The medical power tool system of claim 4, wherein the at least one battery is awakened from its inactive state when the wake mechanism is activated by an end user.

6. The medical power tool system of claim 3, wherein:

the at least one battery is sealed within the sterile exterior housing of the medical power tool;

the at least one battery is entirely enclosed within the sterile exterior housing of the medical power tool.

7. The medical power tool system of claim 6, wherein the medical power tool includes a visual indicator to alert an end user about a status of the at least one battery.

8. The medical power tool system of claim 1, wherein the battery inactive state comprises an ULTRA-LOW POWER mode.

9. The medical power tool system of claim 6, wherein:

the wake mechanism comprises the external charger;

the external charger is external to the sterile exterior housing of the medical power tool.

10. The medical power tool system of claim 6, wherein:

the wake mechanism comprises the external at least one battery;

the external at least one battery is external to the sterile exterior housing of the medical power tool.

11. The medical power tool system of claim 10, wherein the wake mechanism comprises a control board coupled to the at least one battery of the medical power tool and to the external at least one battery.

12. The medical power tool system of claim 11, wherein the wake mechanism comprises at least one contact external to the medical power tool.

13. The medical power tool system of claim 12, wherein:

the medical power tool includes at least one of a drill chuck, a saw blade coupler, or combinations thereof;

the medical power tool includes a trigger to move the at least one of a drill chuck, a saw blade coupler, or combinations thereof;

the wake mechanism does not include the trigger.

14. The medical power tool system of claim 1, wherein:

the at least one battery is sealed within the sterile exterior housing of the medical power tool;

the at least one battery is entirely enclosed within the sterile exterior housing of the medical power tool.

* * * * *